(12) United States Patent
Kido

(10) Patent No.: US 9,518,931 B2
(45) Date of Patent: Dec. 13, 2016

(54) IMAGE INSPECTION APPARATUS, IMAGE INSPECTION METHOD, IMAGE INSPECTION PROGRAM, COMPUTER-READABLE RECORDING MEDIUM AND RECORDING DEVICE

(71) Applicant: Keyence Corporation, Osaka (JP)

(72) Inventor: Manabu Kido, Osaka (JP)

(73) Assignee: Keyence Corporation, Osaka (JP)

( * ) Notice: Subject to any disclaimer, the term of this patent is extended or adjusted under 35 U.S.C. 154(b) by 26 days.

(21) Appl. No.: 14/716,902

(22) Filed: May 20, 2015

(65) Prior Publication Data

US 2015/0355102 A1 Dec. 10, 2015

(30) Foreign Application Priority Data

Jun. 9, 2014 (JP) .................................. 2014-119136

(51) Int. Cl.
*G01N 21/88* (2006.01)
*G06T 7/00* (2006.01)
*G01S 3/786* (2006.01)

(52) U.S. Cl.
CPC ...... *G01N 21/8806* (2013.01); *G01N 21/8851* (2013.01); *G06T 7/0004* (2013.01);
(Continued)

(58) Field of Classification Search
CPC ............ G01N 21/8806; G01N 21/8851; G01N 21/9501; G01N 2021/556; G01N 21/8903; G06K 9/2036; G06K 9/00013; H04N 2201/03112; G06T 2207/10152; G06T 7/0073; G06T 7/004
See application file for complete search history.

(56) References Cited

U.S. PATENT DOCUMENTS 4,899,283 A * 2/1990 Annis .................. G01N 23/046
378/146
6,327,374 B1 * 12/2001 Piironen .............. G01B 11/303
382/108
(Continued)

FOREIGN PATENT DOCUMENTS

JP 2007-206797 8/2007

OTHER PUBLICATIONS

Pernkopf et al., "Image acquisition techniques for automatic visual inspection of metallic surfaces," NDT&E International, vol. 36, 2003, pp. 609-617.

*Primary Examiner* — Jingge Wu
(74) *Attorney, Agent, or Firm* — Kilyk & Bowersox, P.L.L.C.

(57) ABSTRACT

An inspection apparatus includes: an imaging section for capturing a first reference image by simultaneously turning on three or more illumination sections, and a second reference image at imaging timing temporally after the first reference image; a tracking target image designating section for designating a tracking target image in the first reference image and is used for tracking a position of the workpiece; a corresponding position estimating section for searching a position of the tracking target image designated by the tracking target image designating section from the second reference image, and specifying a position including the tracking target image in the second reference image, to estimate a corresponding relation of pixels that correspond among each of the partial illumination images; and an inspection image generating section for generating an inspection image for photometric stereo based on the corresponding relation of each of the pixels of the partial illumination images.

16 Claims, 31 Drawing Sheets

(52) U.S. Cl.
CPC ........ *G06T 7/0073* (2013.01); *G01N 21/8803* (2013.01); *G01N 2201/06* (2013.01); *G01S 3/7864* (2013.01); *G06T 2207/10152* (2013.01); *G06T 2207/30164* (2013.01)

(56) References Cited

U.S. PATENT DOCUMENTS

| | | | | |
|---|---|---|---|---|
| 6,407,373 | B1 * | 6/2002 | Dotan | G01N 21/9501 250/201.3 |
| 6,421,451 | B1 * | 7/2002 | Shiratsuchi | G06K 9/2036 356/613 |
| 6,473,154 | B2 * | 10/2002 | Tabata | G02B 6/00 250/208.1 |
| 6,919,962 | B2 * | 7/2005 | Debevec | G01N 21/55 356/445 |
| 7,844,104 | B2 * | 11/2010 | Tropf | G06K 9/00201 382/153 |
| 7,953,567 | B2 * | 5/2011 | Shimura | G01N 21/94 356/237.2 |
| 8,786,682 | B2 * | 7/2014 | Shpunt | G01B 11/2518 348/50 |

\* cited by examiner

FIG. 19A
MC1 PS1 PS2 PS3 PS4 MC2 PS1' PS2' PS3' PS4' MC3
FIG. 19B
MC1 MC2 PS1 PS2 PS3 PS4 MC1' MC2' PS1' PS2' PS3' PS4'
FIG. 19C
|   | IMAGE INDEX | | | | | | | | |
|---|---|---|---|---|---|---|---|---|---|
|   | 0 | 1 | 2 | 3 | 4 | 5 | 6 | 7 | 8 |
| C | MC1 | PS1 | PS2 | PS3 | PS4 | MC2 | | | |
| D | MC1 | MC2 | PS1 | PS2 | PS3 | PS4 | | | |
| E | MC1 | PS1 | PS2 | MC2 | PS3 | PS4 | MC3 | | |
| F | MC1 | MC2 | PS1 | PS2 | PS3 | PS4 | MC3 | | |
| G | MC1 | PS1 | MC2 | PS2 | MC3 | PS3 | MC4 | PS4 | MC5 |
FIG. 20A
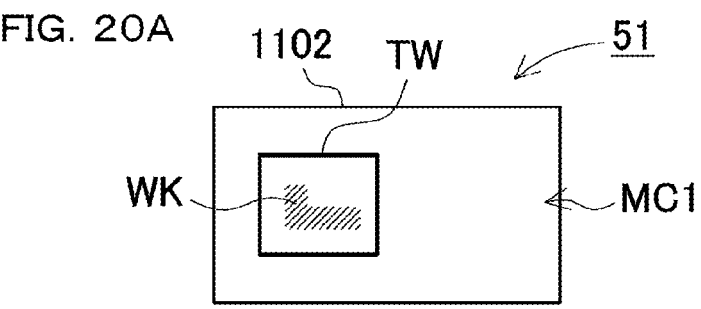
FIG. 20B
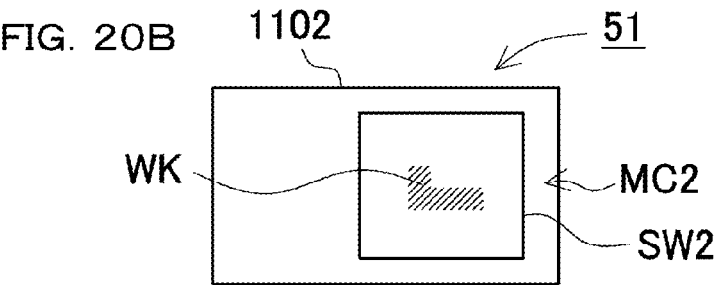

DURING OPERATION

SEARCH INTERPOLATION IN EACH IMAGE IS NOT NEEDED

IMAGE INSPECTION APPARATUS, IMAGE INSPECTION METHOD, IMAGE INSPECTION PROGRAM, COMPUTER-READABLE RECORDING MEDIUM AND RECORDING DEVICE

CROSS-REFERENCE TO RELATED APPLICATIONS

The present application claims foreign priority based on Japanese Patent Application No. 2014-119136, filed Jun. 9, 2014, the contents of which is incorporated herein by reference.

BACKGROUND OF THE INVENTION

1. Field of the Invention

The present invention relates to an image inspection apparatus, an image inspection method, an image inspection program, a computer-readable recording medium and a recording device, each enabling inspection of a flaw and a printed character of a moving workpiece by a photometric stereo method.

2. Description of Related Art

There has been used an image inspection apparatus for performing inspection of the presence or absence of a flaw on the surface of a workpiece, an external shape thereof, and reading of a printed character thereon. Such an image inspection apparatus performs necessary illumination on a workpiece (inspection target or subject), captures its image, and performs image processing such as edge detection on the obtained image data, to perform determination such as defective/non-defective determination based on a result of the processing.

However, in such an image inspection apparatus, there has been a case where the viewing easiness varies by a type of illumination or a direction of applying illumination, depending on a type of the workpiece. For this reason, performing appropriate inspection on such a workpiece has required sufficient information and experiences.

Further, in the conventional image inspection apparatus, erroneous inspection is apt to occur due to a small change in illumination condition, installation condition or the like, and stably performing inspection is difficult, which has been problematic. Further, in visual inspection of the workpiece, although both information on a shape of the workpiece such as a flaw and an edge, i.e., three-dimensional information, and planar information such as a printed character and a stain are inspection targets, those information cannot be detected well in some cases as a result of interference of the information, which has also been problematic.

As a technique for solving such problems, there is known an image processing apparatus for acquiring height information by a photometric stereo method (e.g., see Unexamined Japanese Patent Publication No. 2007-206797). Here, the photometric stereo method is one of techniques for three-dimensional measurement where an image is captured by illumination from a plurality of different illumination directions to find a normal vector of a workpiece from shadow information on the image. An image processing apparatus using such a photometric stereo method creates, from a normal vector (corresponding to an inclination image), an image with components on an X-axis and a Y-axis replaced by a luminance value or a reflectance image (corresponding to an albedo image), and applies the image to image inspection. Here, in order to accurately perform three-dimensional measurement by the photometric stereo method, consideration has been made mainly on a method for installation of an illumination device and a method for irradiation with illumination light.

[Non-patent Document 1] F. Pernkopf, P. O'Leary, "Image acquisition techniques for automatic visual inspection of metallic surfaces", NDT & E International, Elsevier (2003).

The photometric stereo method is normally implemented on the assumption that the position of a plurality of captured images is the same as that of the workpiece. In other words, it is necessary that the workpiece is still and a partial illumination image illuminated from any illumination direction is obtained by capturing the same portion of the same workpiece.

Also in Unexamined Japanese Patent Publication No. 2007-206797 described above, a workpiece not moving but being still is used as a target.

In contrast, in image inspection being used in the field of FA and the like, there are many uses in which image inspection is to be executed on a moving workpiece. For example, when image inspection is to be performed on a workpiece moving on a belt conveyor by the photometric stereo method, the assumption that the position of a plurality of captured images is the same as that of an imaging target is not fulfilled, and hence the method cannot be used as it is.

SUMMARY OF THE INVENTION

The present invention has been made in view of such circumstances, and a principal object is to provide an image inspection apparatus, an image inspection method, an image inspection program, a computer-readable recording medium and a recording device, each enabling inspection of a flaw and a printed character of a moving workpiece by a photometric stereo method.

According to one embodiment of the present invention, an image inspection apparatus is for performing visual inspection of a moving workpiece. The apparatus may include: three or more illumination sections for illuminating a workpiece from mutually different illumination directions; an illumination controlling section for turning on the three or more illumination sections one by one in a predetermined turning-on order or simultaneously turning on the three or more illumination sections; an imaging section for capturing an image of the workpiece from a certain direction at illumination timing for turning on each of the illumination sections by the illumination controlling section, to capture a plurality of partial illumination images with different illumination direction, a first reference image by simultaneously turning on the three or more illumination sections, and a second reference image at imaging timing temporally after the first reference image; a tracking target image designating section for designating a tracking target image which is included in the first reference image and is used for tracking a position of the workpiece; a corresponding position estimating section for searching a position of the tracking target image designated by the tracking target image designating section from the second reference image, and specifying a position including the tracking target image in the second reference image, to estimate a corresponding relation of pixels that correspond among each of the partial illumination images based on the specified position; and an inspection image generating section for generating an inspection image for photometric stereo based on the corresponding relation of each of the pixels of the partial illumination images estimated by the corresponding relation estimating section. With the configuration, even when the workpiece moves and a partial illumination image of the same position cannot be captured, a corresponding position in the partial illumination image can be estimated from the first reference image and the second reference image. Thus, image inspection by photometric stereo processing can be accurately performed on such a moving workpiece.

Further, according to another embodiment of the invention, in the image inspection apparatus, at the time of setting prior to the visual inspection of the moving workpiece, the tracking target image designating section designates a tracking region as the tracking target image from the first reference image, and at the operation time when the visual inspection of the moving workpiece is performed, the corresponding relation estimating section specifies a position of an image corresponding to the tracking region from the second reference image by means of the tracking region, to estimate a position of the tracking region in each of the partial illumination images by use of a relative change between the specified position in the second reference image and a position of the first reference image in which the tracking region is designated.

Further, according to still another embodiment of the present invention, in the image inspection apparatus, at the time of setting prior to the visual inspection of the moving workpiece, the tracking target image designating section designates a pattern region, and at the operation time when the visual inspection of the moving workpiece is performed, the corresponding relation estimating section employs an image included in the pattern region as a tracking target image and specifies a position of the tracking target image from each of the first reference image and the second reference image, to estimate a position of the tracking target image in each of the partial illumination images by use of a relative change between the specified positions of the tracking target images in the first reference image and the second reference image.

Further, according to still another embodiment of the present invention, in the image inspection apparatus, the illumination controlling section completes a cycle of turning-on timing for each of the illumination sections so as to capture, by the imaging section, partial illumination images illuminated from different illumination directions at successive imaging timing, controls the turning-on timing for each of the illumination sections so as to capture reference images before and after the completed cycle of the illumination timing, and controls each of the turning-on timing so as to have a regular interval, and the imaging section synthesizes the imaging timing with the turning-on timing controlled by the illumination controlling section.

Further, according to still another embodiment of the present invention, the image inspection apparatus may further include a position displacement amount setting section for setting an assumed position displacement amount between the workpiece and a linearly interpolated workpiece, or an angle displacement amount setting section for setting an assumed angle displacement amount between the workpiece and a linearly interpolated workpiece.

Further, according to still another embodiment of the present invention, in the image inspection apparatus, the reference image may be an entirely turning-on image captured by the imaging section in a state where all the illumination sections are turned on.

Further, according to still another embodiment of the present invention, in the image inspection apparatus, when the number of the illumination sections is N, illumination light of each of the illumination sections may be adjusted to be 1/N at the time of turning on all of the illumination sections so as to capture an entirely turning-on image Further, according to still another embodiment of the present invention, in the image inspection apparatus, the number of the illumination sections may be four, and illumination light of each of the illumination sections may be adjusted to be ¼ at the time of turning on all of the four illumination sections for capturing an entirely turning-on image.

Further, according to still another embodiment of the present invention, in the image inspection apparatus, the inspection image generating section may include a normal vector calculating section for calculating a normal vector with respect to the surface of the workpiece at each of pixels by a photometric stereo method by use of a pixel value of each of the pixels having the corresponding relation among the plurality of partial illumination images captured by the imaging section, and a contour image generating section for performing differential processing in an X-direction and a Y-direction on the normal vector at each of the pixels calculated by the normal vector calculating section, to generate a contour image that shows a contour of inclination of the surface of the workpiece.

Further, according to still another embodiment of the present invention, the image inspection apparatus according to the ninth aspect may further include: an inspection region specifying section for specifying a position of an inspection region as an inspection target from the contour image generated by the contour image generating section; an image processing section for performing image processing for detecting abnormality in the inspection region specified by the inspection region specifying section; and a determination section for determining a presence or absence of a flaw on the surface of the workpiece based on a result of the processing by the image processing section.

Further, according to still another embodiment of the present invention, the image inspection apparatus may further include: a texture extraction image generating section for calculating, from a normal vector at each of the pixels which exists in number corresponding to the number of times of illumination performed by the illumination sections and is calculated by the normal vector calculating section, albedos of each of the pixels in the same number as the number of the normal vectors, to generate from the albedos a texture extraction image that shows a design obtained by removing an inclined state of the surface of the workpiece, and the contour image generating section and the texture extraction image generating section may be configured to be switchable.

Further, according to still another embodiment of the present invention, in the image inspection apparatus, the tracking target image may be an image including the workpiece.

Further, according to still another embodiment of the present invention, in the image inspection apparatus, the normal vector calculating section may calculate a normal vector with respect to a workpiece moving at a uniform speed by the photometric stereo method.

Further, according to still another embodiment of the present invention, in the image inspection apparatus, the normal vector calculating section may calculate a normal vector with respect to a workpiece moving in an X-Y direction by the photometric stereo method.

According to one embodiment of the present invention, an image inspection method is for capturing an image of a moving workpiece to perform visual inspection. The method may include: simultaneously turning on three or more illumination sections at first reference timing, and capturing an image of the workpiece by a common imaging section whose imaging direction and relative position with the illumination section are adjusted in advance, to acquire a first reference image; turning on the three or more illumination sections one by one in a predetermined turning-on order, illuminating, from mutually different illumination directions at different turning-on timing, the workpiece moved from the time point of the first reference timing, and capturing one partial illumination image with respect to each illumination direction by the imaging section, to acquire a plurality of partial illumination images with different illumination directions; simultaneously turning on the three or more illumination sections at second reference timing, and capturing, by the imaging section, an image of the workpiece further moved from the time point of each of the turning-on timing, to acquire a second reference image; designating by a tracking target image specifying section a tracking target image which is included in the first reference image and is used for tracking a position of the workpiece; searching the tracking target image designated by the tracking target image designating section from the second reference image, and specifying a position including the tracking target image in the second reference image, to estimate a corresponding relation of pixels that correspond among each of the partial illumination images based on the specified position; generating an inspection image for photometric stereo by an inspection image generating section based on the estimated corresponding relation of each of the pixels of the partial illumination images; and performing visual inspection of the workpiece by use of the inspection image.

Further, according to one embodiment of the present invention, an image inspection program is for capturing an image of a moving workpiece to perform visual inspection. The program may allow a computer to realize functions of; simultaneously turning on three or more illumination sections at first reference timing, and capturing an image of the workpiece by a common imaging section whose imaging direction and relative position with the illumination section are adjusted in advance, to acquire a first reference image; turning on the three or more illumination sections one by one in a predetermined turning-on order, illuminating, from mutually different illumination directions at different turning-on timing, the workpiece moved from the time point of the first reference timing, and capturing one partial illumination image with respect to each illumination direction by the imaging section, to acquire a plurality of partial illumination images with different illumination directions; simultaneously turning on the three or more illumination sections at second reference timing, and capturing, by the imaging section, an image of the workpiece further moved from the time point of each of the turning-on timing, to acquire a second reference image; designating a tracking target image which is included in the first reference image and is used for tracking a position of the workpiece; searching the designated tracking target image from the second reference image, and specifying a position including the tracking target image in the second reference image, to estimate a corresponding relation of pixels that correspond among each of the partial illumination images based on the specified position; generating an inspection image for photometric stereo by an inspection image generating section based on the estimated corresponding relation of each of the pixels of the partial illumination images; and performing visual inspection of the workpiece by use of the inspection image.

Further, according to one embodiment of the present invention, a computer-readable recording medium or a recording device is for storing the image inspection program. The recording medium includes a magnetic disk, an optical disk, a magneto-optical disk, a semiconductor memory, and other program-storable medium, such as a CD-ROM, a CD-R, a CD-RW, a flexible disk, a magnetic tape, an MO, a DVD-ROM, a DVD-RAM, a DVD-R, a DVD+R, a DVD-RW, a DVD+RW, a Blu-ray (product name), and an HD-DVD (AOD). Further, the program is distributed by downloading through a network such as the Internet, other than stored into the above recording medium and distributed. Moreover, the recording device includes a general-purpose or special-purpose device where the program is mounted in the form of software, firmware or the like, in an executable state. Furthermore, each processing and each function included in the program may be executed by program software that is executable by the computer, and processing of each part may be realized by predetermined hardware such as a gate array (FPGA, ASIC) or in the form of program software being mixed with a partial hardware module that realizes some element of hardware.

BRIEF DESCRIPTION OF THE DRAWINGS

FIG. 19A is a diagram showing the timing for capturing MC1, PS1, PS2, PS3, PS4 and MC2 in an interpolation-linear interpolation method, FIG. 19B is a diagram showing the timing for capturing MC1, PS1, PS2, PS3, PS4 and MC2 in an extrapolation-linear interpolation, and FIG. 19C are diagrams showing a plurality of modified examples of the timing for capturing MC images;

FIG. 20A is a schematic view showing a state where a tracking region TW is set on the MC1 image, and FIG. 20B is a state where a search region SW2 is set on the MC2 image, at the time of setting of a tracking region designating method;

DETAILED DESCRIPTION OF PREFERRED EMBODIMENTS

Hereinafter, embodiments of the present invention will be described with reference to the drawings. The embodiments shown below are for embodying technical ideas of the present invention, and the present invention is not limited to the following. Further, the present specification does not limit members shown in the claims to members of the embodiments. Especially, dimensions, materials, shapes, relative disposition and the like of constituent components described in the embodiments are not intended to restrict the scope of the present invention thereto, but are mere explanatory examples, unless particularly specifically described. It is to be noted that sizes, positional relations and the like of members shown in each drawing may be exaggerated for clarifying a description. Further, in the following description, the same name or symbol denotes the same member or members of the same quality, and a detailed description thereof will be omitted as appropriate. Moreover, each element constituting the present invention may have a mode where a plurality of elements are made up of the same member and the one member may serve as the plurality of elements, or conversely, a function of one member can be shared and realized by a plurality of members.

(1. Configuration of Image Inspection Apparatus 1)

Figure 1:
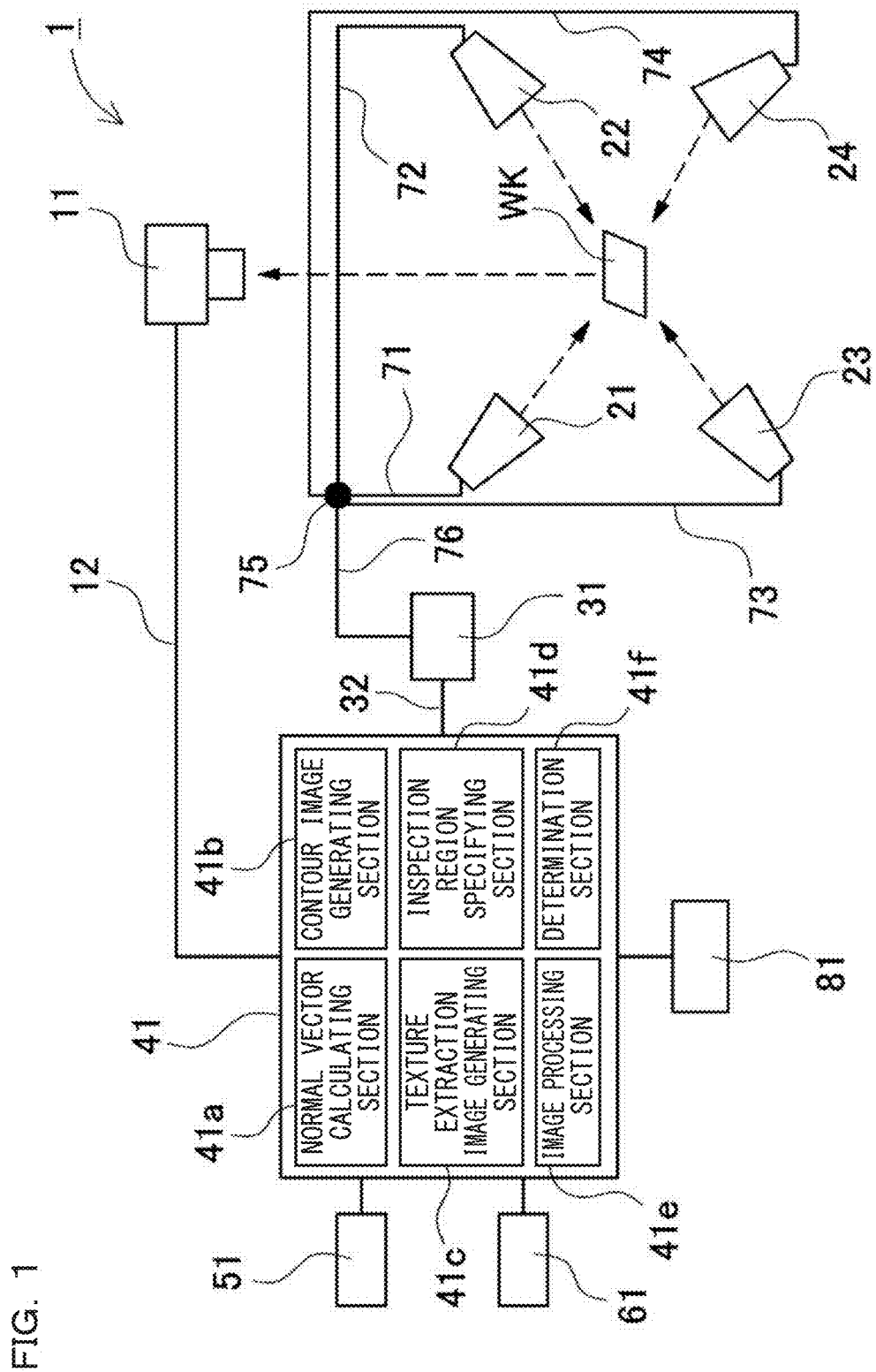
FIG. 1 is a block diagram showing a configuration of an image inspection apparatus according to a first embodiment of the present invention.

FIG. 1 shows a block diagram of an image inspection apparatus according to a first embodiment of the present invention. The image inspection apparatus 1 shown in this drawing includes: an imaging section 11 that captures an image of a workpiece WK from a certain direction; illumination sections for illuminating the workpiece WK from three or more different illumination directions; an illumination controlling section 31 for turning on each of the illumination sections one by one in a turning-on order; and an image processing part 41 that is connected with the illumination controlling section and the imaging section to control these sections. The image processing part 41 and the imaging section are connected via an image capturing cable 12, and the image processing part 41 and the illumination controlling section 31 are connected via an illumination cable 32. Further, the image processing part connects a display section 51 and an operation section 61. Moreover, the image processing part can also be connected with a PLC (Programmable Logic Controller), a computer and the like as external devices, according to the need.

The imaging section captures an image of the workpiece WK from a certain direction at illumination timing for turning on each of the illumination sections by the illumination controlling section, to capture a plurality of partial illumination images with different illumination directions.

The image processing part functions as a source image generating section for generating a source image of the surface of the workpiece in an assumed illumination direction, obtained by assuming an illumination direction, based on a photometric stereo method by use of a pixel value of each of the pixels having the corresponding relation among the plurality of partial illumination images captured by the imaging section, in each of a plurality of different assumed illumination directions. The source image generating section specifically realizes functions of a normal vector calculating section 41a, a contour image generating section 41b, a texture extraction image generating section 41c, an inspection region specifying section 41d, an image processing section 41e, and a determination section 41f. The normal vector calculating section 41a calculates a normal vector n with respect to the surface of the workpiece WK at each of pixels by use of a pixel value of each of pixels having a corresponding relation among the plurality of partial illumination images captured by the imaging section. The contour image generating section 41b performs differential processing in an X-direction and a Y-direction on the calculated normal vector n at each of the pixels, to generate a contour image that shows a contour of inclination of the surface of the workpiece WK. The texture extraction image generating section 41c calculates, from the calculated normal vector n at each of the pixels which exists in number corresponding to the number of times of illumination performed by the illumination section, an albedo of each of the pixels, to generate from the albedos a texture extraction image that shows a design obtained by removing an influence of inclination of the surface of the workpiece WK. The inspection region specifying section 41d specifies a position of an inspection region to become an inspection target with respect to the generated contour image. The image processing section 41e performs image processing for detecting a flaw within the specified inspection region. The determination section 41f determines the presence or absence of a flaw on the surface of the workpiece WK based on the processing result.

The imaging section and the illumination section can be arranged as separate members. This allows a layout with a high degree of freedom. As one example shown in a schematic plan view of FIG. 2 and a schematic side view of FIG. 3, the imaging section 11 with an optical axis turned in a vertical direction is arranged immediately above the workpiece WK placed on a stage SG. Further, four illumination sections, namely a first illumination section 21, a second illumination section 22, a third illumination section 23 and a fourth illumination section 24, are arranged at the same height in the cardinal directions of north, south, east and west of the imaging section 11. A positional relation between the imaging section and each of the illumination sections having been arranged are recorded on the image inspection apparatus. Each of the illumination sections is sequentially turned on at predetermined illumination timing by the illumination controlling section, and an image of the workpiece is captured from a certain direction by the common imaging section, to acquire partial illumination images.

It is to be noted that the configuration where the imaging section and the illumination section are separate members is not restrictive, and these may be integrally configured via an arm or the like. In this case, since the positional relation between the imaging section and each of the illumination sections is fixed in advance, an adjustment operation such as matching of the optical axes can be made unnecessary. However, the degree of freedom is lost in this configuration.

(Imaging Section)

As for the imaging section 11, for example, an image capturing element such as a CCD (Charge Coupled Device) camera or a CMOS (Complementary Metal Oxide Semiconductor) imager can be used. The image capturing element performs photoelectric conversion on an image of a subject to output an image signal, and a signal processing block converts the outputted image signal to a luminance signal and a color difference signal, to output the signals to the image processing part 41 connected by the image capturing cable 12.

(Illumination Section)

Figure 2:
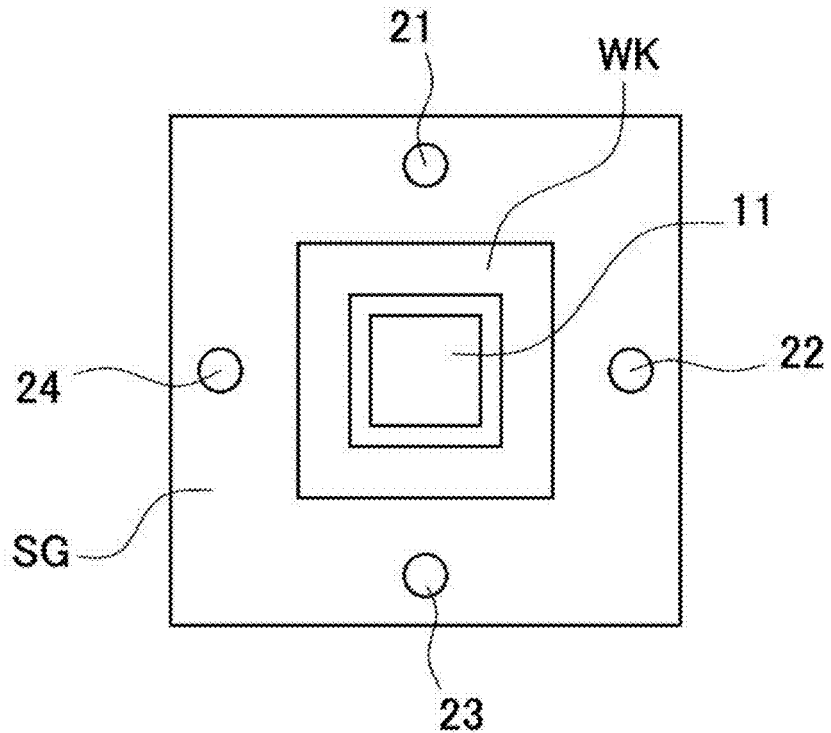
FIG. 2 is a schematic plan view showing a positional relation between an imaging section and each of illumination sections of the image inspection apparatus of FIG. 1.

The illumination sections 21, 22, 23, 24 are arranged so as to surround the workpiece WK as shown in the schematic plan view of FIG. 2 such that the workpiece WK can be irradiated with illumination light from different illumination directions. Further, as shown in the schematic side view of FIG. 3, each of the illumination sections is arranged with the optical axis turned obliquely below. It is preferable to match the optical axis of the imaging section with a central axis of a plane (imaginary rotational plane) provided with the illumination sections so that an image of the workpiece illuminated by each of the illumination sections can be captured by the common imaging section. Further, it is preferable to set an interval (azimuth from the central axis) between the illumination sections by uniformly dividing 360° by the number of illumination sections. Moreover, it is preferable to make a zenith angle constant in all the illumination sections. Furthermore, it is also preferable to make a distance between each of the illumination sections and the workpiece constant. This can simplify input of information on the azimuth and the zenith angle which are required for computing in photometric stereo processing. Further, as described later, since an entirely turning-on image MC is captured in an entirely turning-on state where all the illumination sections are on, imaging can be performed in an illumination state with little unevenness just by uniformly reducing the intensity of the entire illumination with the above configuration.

In the example of FIG. 1, the illumination sections are made up of four sections: the first illumination section 21, the second illumination section 22, the third illumination section 23 and the fourth illumination section 24. For each of the illumination sections, an incandescent light bulb, a fluorescent lamp or the like can be used. In particular, a semiconductor light-emitting element such as a light emitting diode (LED) is preferable as having small power consumption, a long life and excellent responsiveness. As shown in FIG. 1, the illumination sections are connected to an illumination dividing unit 75 via the respective cables 71, 72, 73, 74, and are further connected to the illumination controlling section 31 via a cable 76.

(Illumination Dividing Unit)

The illumination dividing unit is an interface for connecting each of the illumination sections and the illumination controlling section. Specifically, an illumination connector for connecting the illumination cable extending from the illumination section is provided. In the example of FIG. 1, four illumination connectors are provided so as to connect the four illumination sections. Here, in order to correctly connect the illumination cable to the illumination connector, a mark or the like may be provided as an installation auxiliary section. Correctly connecting the illumination cable of each of the illumination sections to the illumination connector of the illumination dividing unit allows the illumination section to be turned on from a correct direction in a correct order by the illumination controlling section, and further, operating the imaging section in synchronization with each illumination timing allows the partial illumination image to be captured. In addition, although the illumination dividing unit is provided as a separate body from the illumination controlling section in the example of FIG. 1, this configuration is not restrictive, and for example, the illumination dividing unit may be incorporated into the illumination controlling section.

An illumination color of each of the illumination sections 21, 22, 23 24 can also be changed in accordance with a type of the workpiece WK. For example, when a small flaw is to be inspected, blue illumination with a short wavelength is preferable. When a colored workpiece is to be inspected, white illumination is preferably used so that the color of the illumination does not become obstructive. When oil is on the workpiece, red illumination may be adopted for preventing an influence thereof.

Figure 3:
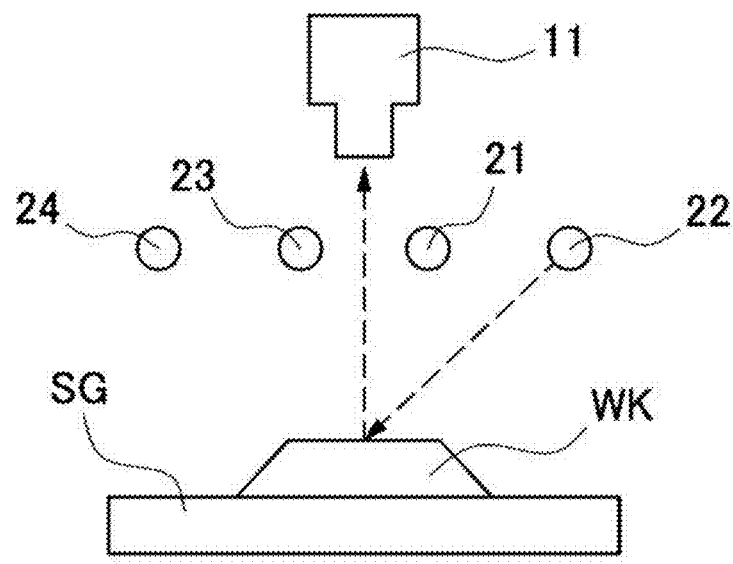
FIG. 3 is a schematic side view showing the positional relation between the imaging section and each of the illumination sections of the image inspection apparatus of FIG. 1.

Although the number of illumination sections is four in the example of FIGS. 1 to 3, at least three illumination sections can be sufficiently used so as to allow the workpiece WK to be illuminated from three or more different illumination directions. When the number of illumination sections is increased, the partial illumination images from more illumination directions can be obtained, and hence the accuracy in image inspection can be improved. For example, directions of northeast, northwest, southeast and southwest may be added and a total of eight illumination sections may be arranged. Further, it is preferable to set an interval (azimuth from the central axis) between the illumination sections by uniformly dividing 360° by the number of illumination sections. Moreover, it is preferable to make a zenith angle constant in all the illumination sections. It is to be noted that an increase in number of images to be processed leads to an increase in processing amount, which slows the processing time. In the present embodiment, in view of balance of the processing speed, the easiness to perform the arithmetic processing, the accuracy and the like, the number of illumination sections is set to four as described above.

Figure 4:
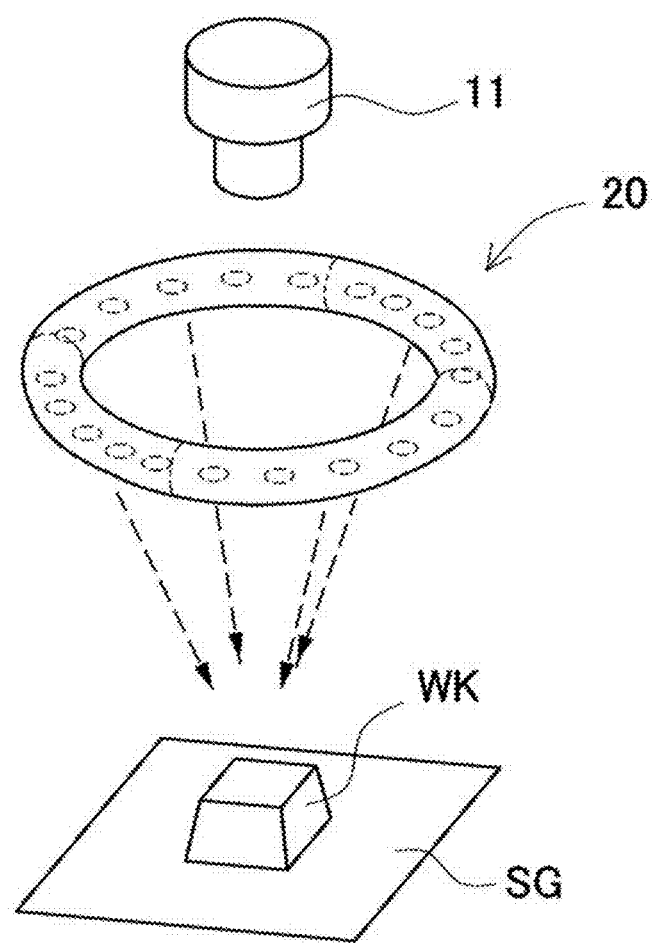
FIG. 4 is a schematic view showing an illumination section that realizes four illumination blocks according to a second embodiment.

Further, the illumination section can also be made up of a plurality of annularly arranged light-emitting elements. For example, in ring illumination according to a second embodiment shown in FIG. 4, annularly arranged light-emitting elements are divided into four illumination blocks. Then, the illumination controlling section takes a first illumination block as the first illumination section, a second illumination block as the second illumination section, a third illumination block as the third illumination section and a fourth illumination block as the fourth illumination section, and makes illumination timing for the respective illumination blocks different, thereby allowing control in a similar manner to the case of four separate illumination sections existing.

Figure 5:
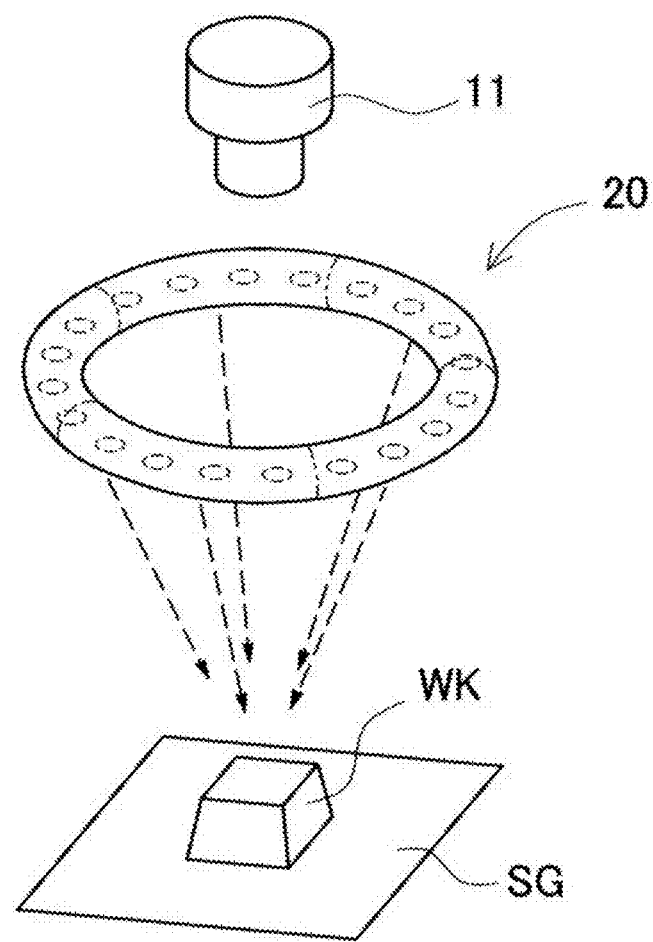
FIG. 5 is a schematic plan view showing a state where five illumination blocks are realized by the illumination section of FIG. 4.

Further, with this configuration, there can be obtained an advantage that the number of illumination sections can be arbitrary changed by use of the same ring illumination. That is, when turning-on of each of the light-emitting elements can be arbitrarily controlled by the illumination controlling section, as shown in FIG. 5, the number of illumination blocks obtained by dividing the circumference of the annularly arrayed light-emitting elements is changed from four to five, and the illumination controlling section performs control so as to capture each of partial illumination images by shifting the illumination timing for turning on each of the five illumination blocks. Thus, it is possible to acquire partial illumination images from five illumination directions. Further, similarly, when the annular circumference is divided into six or seven blocks, the illumination directions can further be increased. Moreover, the configuration where partial illumination images are constantly acquired by certain illumination blocks is not restrictive, and illumination blocks may be changed in each cycle. As thus described, by adjusting the turning-on pattern of each of the light-emitting elements, it is possible to virtually change the number of illumination blocks by use of the same one ring illumination, so as to obtain a similar effect to that obtained by adjusting the number of illumination sections. In other words, it is possible to deal with different accuracies by means of the common hardware.

Figure 6:
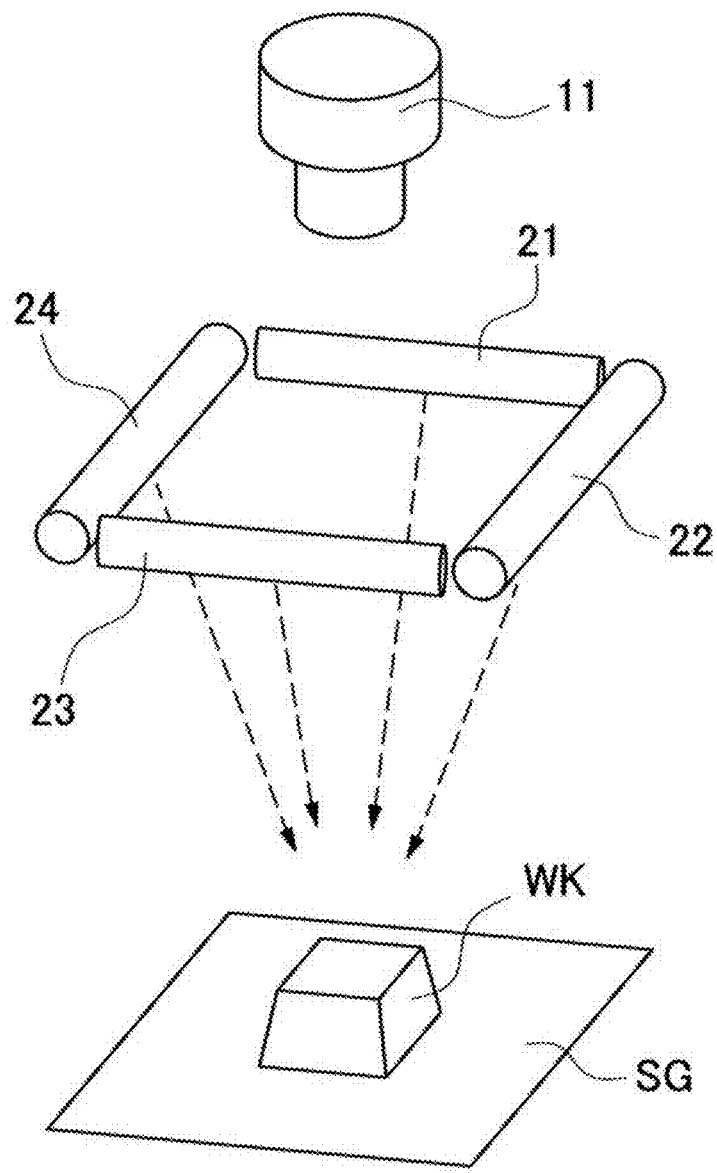
FIG. 6 is a schematic plan view showing illumination sections according to a third embodiment.
Figure 7:
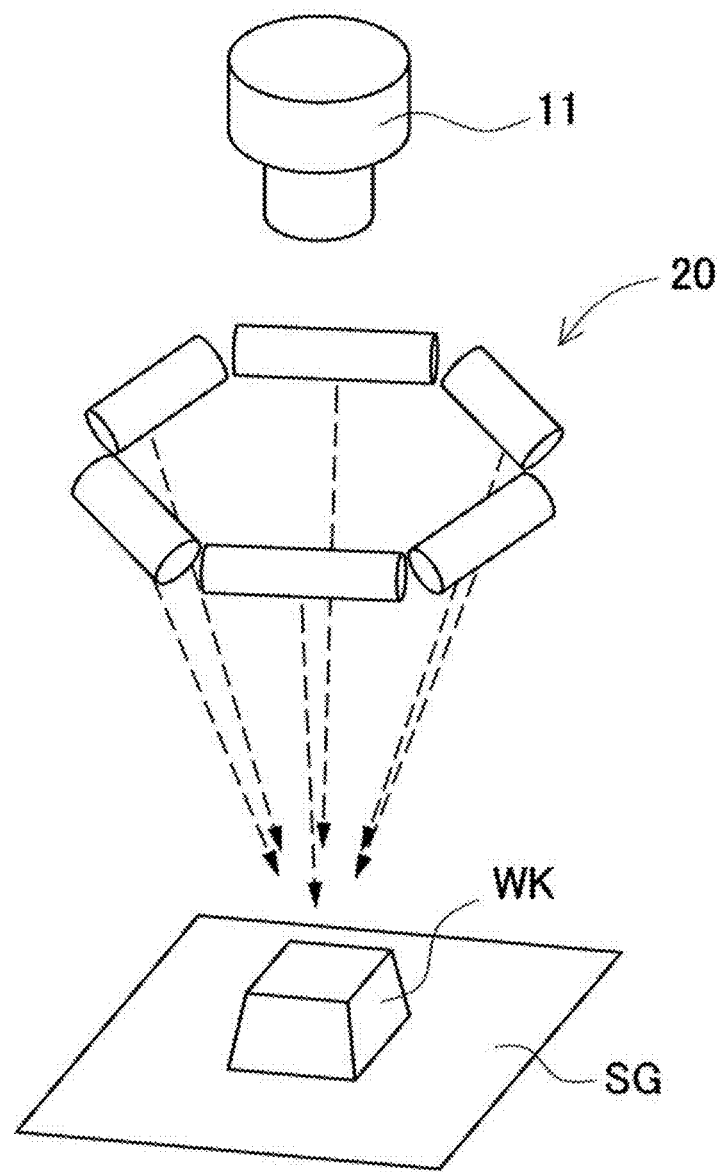
FIG. 7 is a schematic plan view showing illumination sections according to a fourth embodiment.

Further, other than arranging the illumination sections in the annular form, it is also possible to arrange illumination sections, each of which is configured in a bar shape, in a rectangular form as a third embodiment as shown in a schematic plan view of FIG. 6, or it is also possible to arrange illumination sections in a polygonal form as a fourth embodiment as shown in a schematic plan view of FIG. 7.

Figure 8:
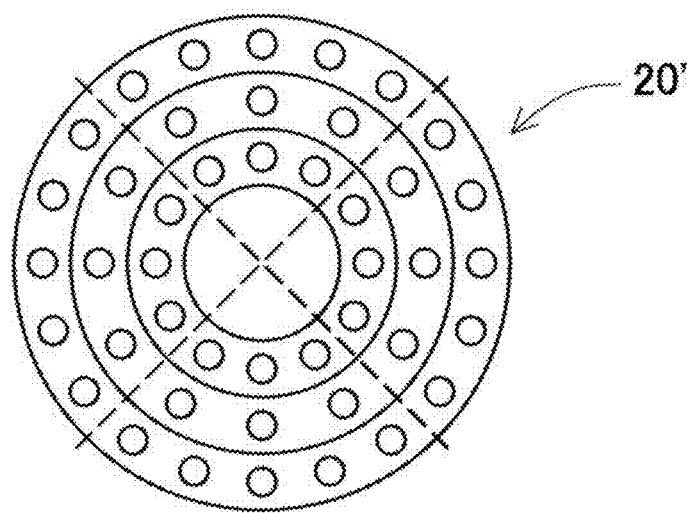
FIG. 8 is a schematic plan view showing an illumination section according to a modified example.
Figure 9:
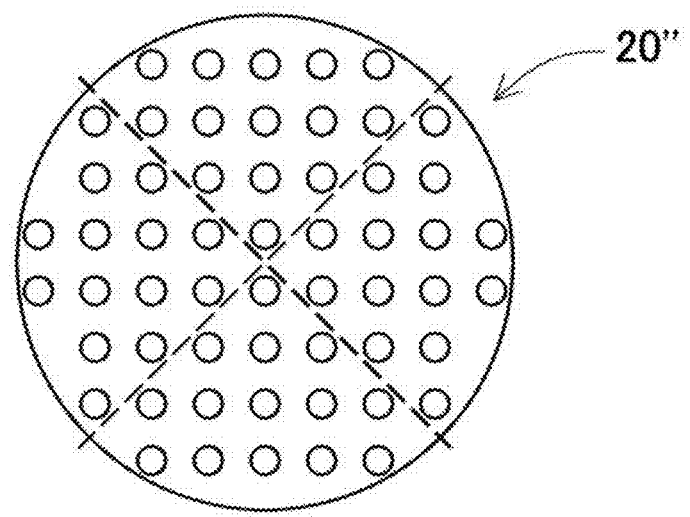
FIG. 9 is a schematic plan view showing an illumination section according to another modified example.

Alternatively, it is also possible to arrange the illumination sections in a flat form other than being arranged in a circular or polygonal annular form. For example, a large number of light-emitting elements are arranged in a flat form and an illumination block to be turned on is changed, thereby allowing realization of different illumination directions. Specifically, as an illumination section according to a modified example shown in FIG. 8, an illumination unit 20' obtained by superimposing concentrically annular rings is configured, and the illumination section is configured by the annular rings with different radiuses as respective illumination blocks. Alternatively, as an illumination section according to another modified example shown in FIG. 9, an illumination unit 20" obtained by arraying light-emitting elements in a dot-matrix form may be configured, and the illumination section may be configured by illumination blocks obtained by dividing the illumination unit by a plurality of line segments passing through its center. As thus described, the illumination section and the illumination direction in the present invention are not restricted to physically separated illumination, but are used in the meaning of including a configuration where illumination is performed by means of illumination blocks obtained by dividing one illumination section into a plurality of blocks.

It is to be noted that in the present example, the processing is performed on the assumption that partial illumination light by each of the illumination sections is parallel light within an imaging range. So long as the partial illumination light is parallel light, only the direction of the illumination light (e.g., any of north, south, east and west) is a concern, and other detailed positions, such as a coordinate position of a light source of the illumination section, are not required to be considered.

(Illumination Controlling Section)

The illumination controlling section performs control so as to turn on three or more illumination sections one by one in a turning-on order or turn them on simultaneously, and synthesize each of the illumination sections and the imaging section such that an image of the workpiece is captured by the imaging section from a certain direction at illumination timing for turning on each of the illumination sections. In other words, the illumination controlling section synthesizes the timing for illumination by the illumination section with the timing for imaging by the imaging section. Further, the turning-on order in which the illumination controlling section turns on each of the illumination sections may be such that the illumination sections arranged to surround the workpiece are turned on in a clockwise order or a counterclockwise order, or in a discrete order such as an alternate order or a crossing order. Whatever the order is, it is possible to construct a normal vector image by the photometric stereo method, by grasping an illumination direction of illumination by which a partial illumination image has been captured at each illumination timing.

Figure 10:
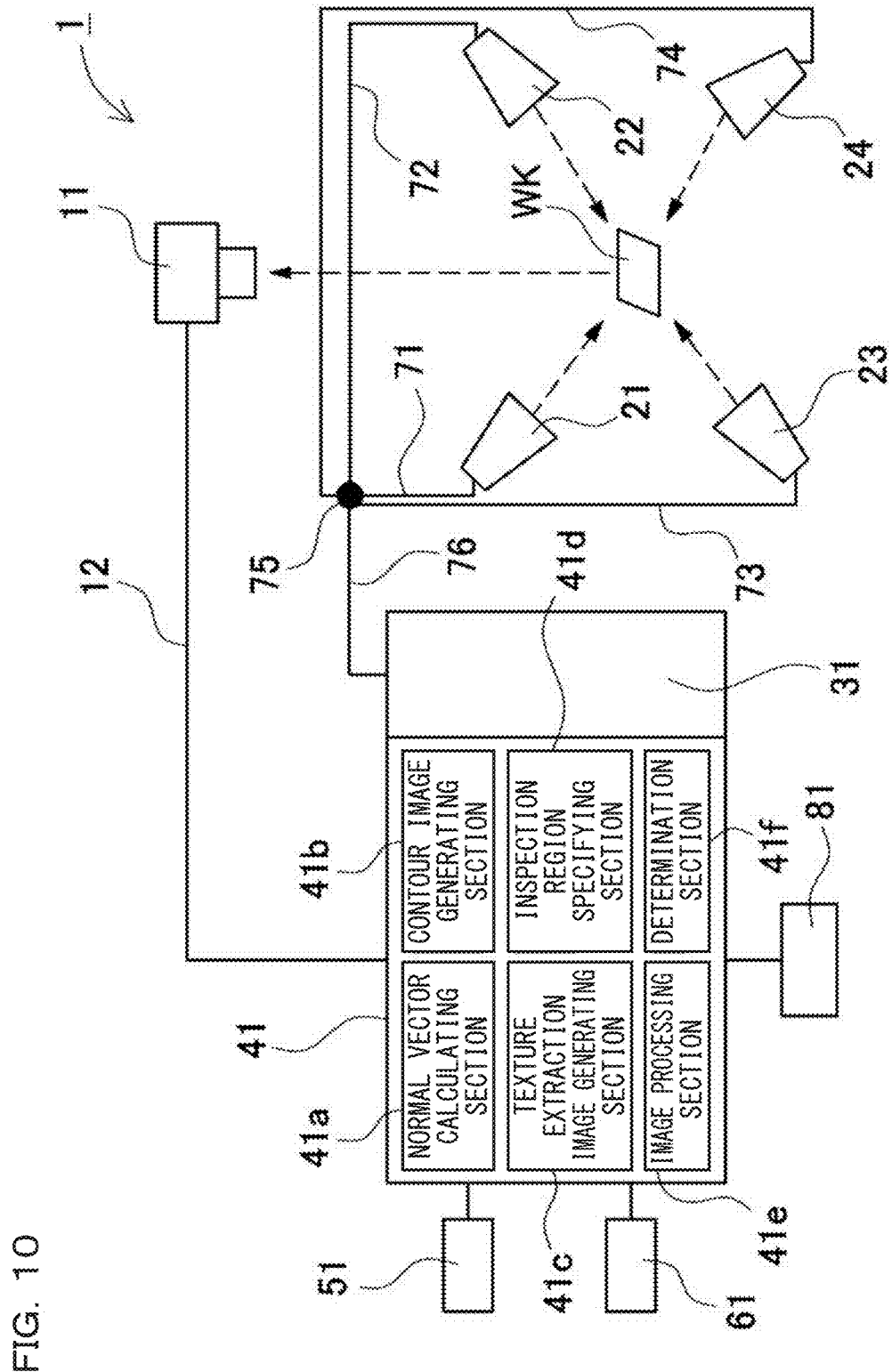
FIG. 10 is a schematic view showing a configuration of an image inspection apparatus according to a fifth embodiment.
Figure 11:
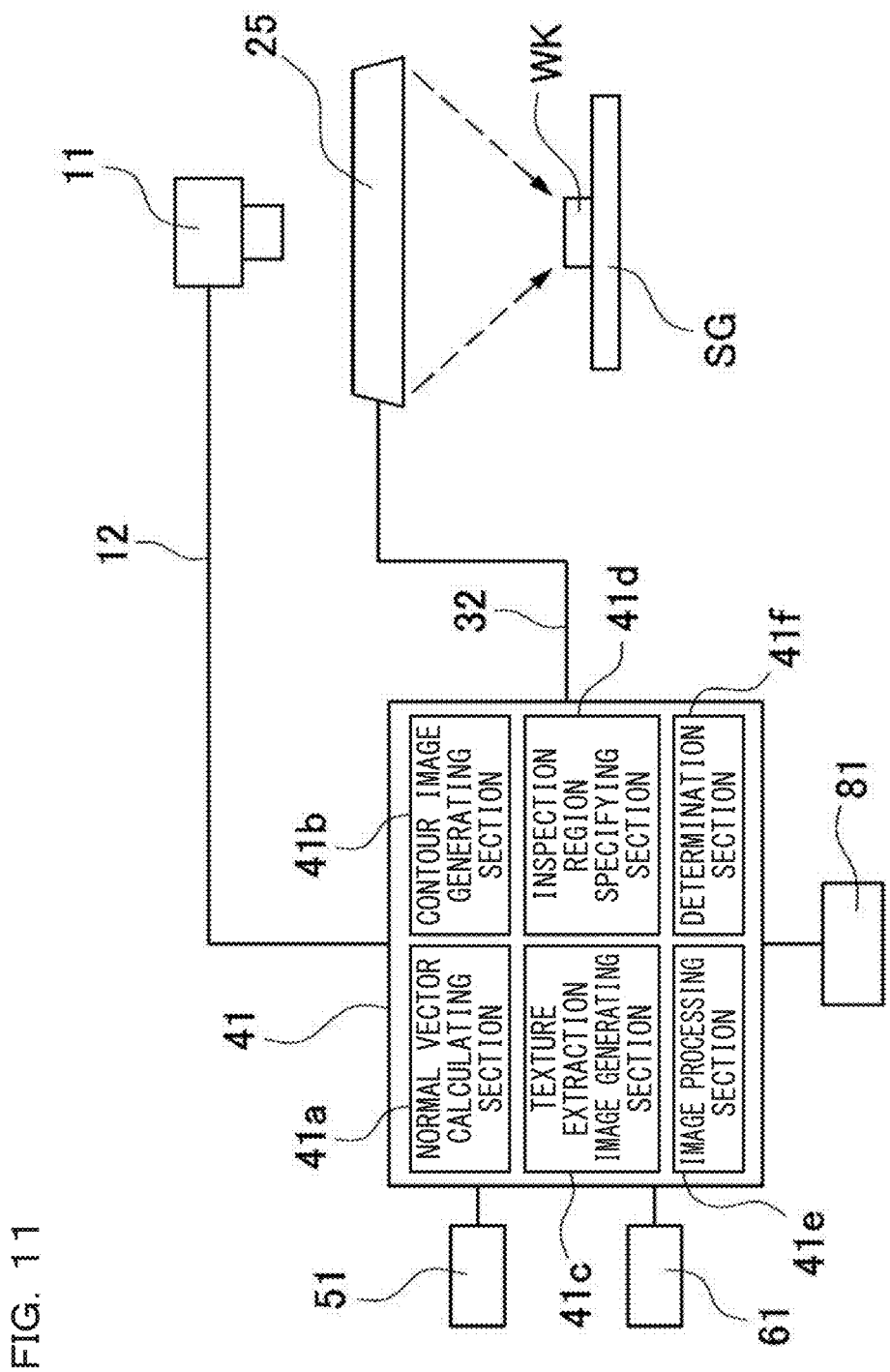
FIG. 11 is a schematic view showing a configuration of an image inspection apparatus according to a sixth embodiment.

It is to be noted that in the first embodiment of FIG. 1, the illumination controlling section 31 is provided as a separate body from the image processing part 41, but this configuration is not restrictive. For example, the illumination controlling section 31 may be integrated with the image processing part 41 as in a fifth embodiment shown in FIG. 10, or it may be built in an illumination section 25 as in a sixth embodiment shown in FIG. 11.

(Image Processing Part)

The image processing part 41 controls operations of the imaging section 11 and the illumination sections 21, 22, 23, 24. Further, by use of image signals Q1 to Q4 of four partial illumination images inputted from the imaging section 11, the image processing part 41 generates a normal vector image (hereinafter referred to as "inclination image") on a plane at each pixel, and creates, from the inclination image, a secondary inclination image (hereinafter referred to as "contour extraction image") in the X-direction and the Y-direction, and an albedo (meaning a reflectance) image (hereinafter also referred to as "texture extraction image"). Then, by use of those images, the image processing part 41 performs processing for inspecting a flaw, detecting a character, or the like. It should be noted that the processing for inspecting a flaw, detecting a character, or the like is not restricted to the configuration where the processing is performed in the image processing part 41, and for example, it can be executed on the external device side such as a PLC 81.

Figure 12:
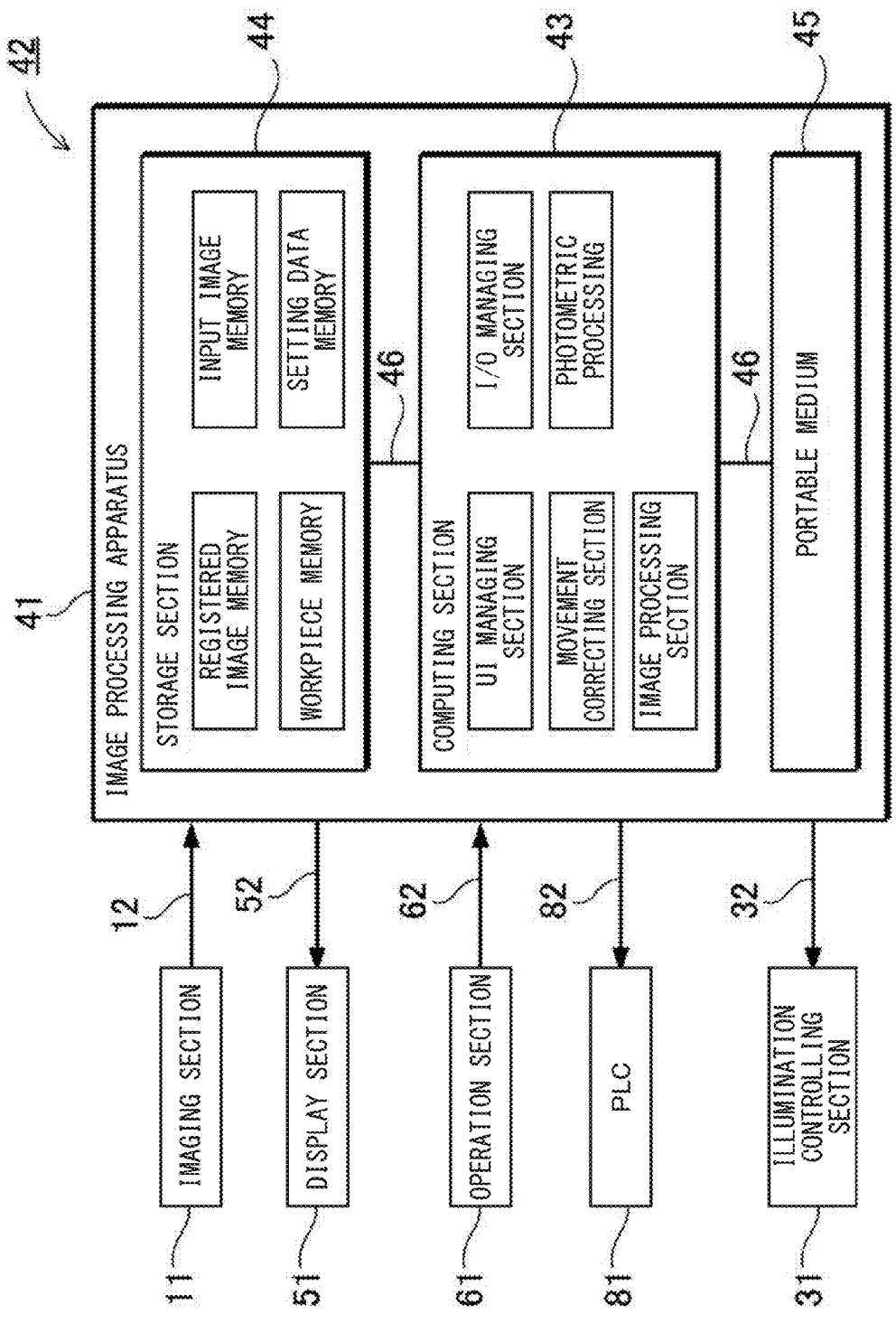
FIG. 12 is a block diagram for use in explaining a signal processing system of an image processing section.

FIG. 12 shows a signal processing system 42 of the image processing part 41. The signal processing system 42 is made up of a CPU 43, a memory 44, a ROM 45, a display section 51, an operation section 61 such as a pointing device, the imaging section 11, the illumination controlling section 31, and a PLC (program logic controller) 81 for executing result output processing, and these are mutually connected via a bus 46 and cables 12, 32, 52, 62 and 82. It is to be noted that the ROM 45 may be a portable medium. Further, the display section 51 may be used together with the operation section 61 by forming a touch panel or the like.

Based on a program stored in the ROM 45, the CPU 43 controls transmission and reception of data among the memory 44, the ROM 45, the display section 51, the operation section 61, the imaging section 11, the illumination controlling section 31 and the PLC 81, and controls the display section 51, the imaging section 11 and the illumination controlling section 31.

Although the image processing part 41 is assumed to be, for example, one computer stored with a program, but each section may be configured by combination of a plurality of computers, or part of the sections may be configured of a dedicated circuit. Alternatively, the image processing part 41 can be a dedicatedly designed member such as an ASIC.

(Determination Section)

The image processing part 41 realizes the function of the determination section as described above. The determination section inspects the presence or absence of a flaw or a size of the flaw based on the obtained texture extraction image. For example, when the obtained value is not smaller than a predetermined threshold, determination as a flaw is made. Further, according to the need, the determination section can also perform OCR based on a contour extraction image, to output a recognized character string.

(Basic Principle)

Next, by use of the above image inspection apparatus, a basic principle in performing visual inspection of the workpiece will be described while it is compared with the technique of Unexamined Japanese Patent Publication No. 2007-206797 as the conventional technique. First, a basic principle of the technique disclosed in Unexamined Japanese Patent Publication No. 2007-206797 is that by use the principle of the photometric stereo method, light is applied to an unknown surface from a variety of directions and the shape of the workpiece is estimated using differences in reflective light of the workpiece. The reflective light of the workpiece is affected by an incident angle of illumination, a distance from illumination and the like, and has a property that the light is brightest when the incident angle is 90° and the light becomes darker as the distance from the illumination becomes longer.

With this property, a plurality of illuminations whose brightness and positions are known are prepared and turning-on of the illumination is sequentially switched, to estimate in which direction the surface is turned by use of a difference in brightness of the reflective light at the time of irradiation with light from the illumination in each direction. Specifically, an X-component image obtained by replacing the X-component and the Y-component of the inclination image with luminance of the X-component, and a Y-component image obtained by replacing the X-component and the Y-component of the inclination image with luminance of the Y-component are to be created and applied to inspection.

However, this method has a problem of inferior robust characteristics because an obtained inspection image greatly changes by slight inclination of the illumination or the installation surface of the workpiece, or an error of input information such as an originally inputted illumination position. For example, the method has a disadvantage that an inspection image corresponding to an actual shape of the workpiece can not necessarily be obtained, as seen in a case where an image of roughness is obtained although there actually is no roughness, and a case where an image in which the center of the workpiece is swelled due to a change in brightness is seen while a closer position of an image to illumination is normally seen more brightly.

In contrast, a basic principle of the image inspection technique according to the present embodiment is as follows. Although a primary inclination image is generated by the photometric stereo method at first, a secondary inclination image, namely a contour extraction image is created by performing differential processing on the generated primary inclination image in the X-direction and the Y-direction, and inspection of a flaw and the like is performed with that image. Even in the case of occurrence of the foregoing disadvantage, the influence on the secondary inclination image is small, and by setting a place with a large change in surface inclination to have a dark tone and setting a place with a small change in surface inclination to have a bright tone, the secondary inclination image becomes a preferable image for extracting a flaw, a contour and the like where the inclination of the surface of the workpiece greatly changes.

Further, in the technique disclosed in Unexamined Japanese Patent Publication No. 2007-206797, halation occurs in the reflectance image (corresponding to the texture extraction image) generated by the photometric stereo method, and it may be difficult to detect a character, and the like. In contrast, in the image inspection technique according to the present embodiment, by use of the basic principle that halation basically does not occur in the same place unless two illuminations are used, for example, the third largest pixel value of four pixel values is adopted at each pixel, to remove an influence of halation.

Additionally, in the image processing apparatus disclosed in Unexamined Japanese Patent Publication No. 2007-206797, the camera and the light source for illumination are integrally configured, but with this configuration, the camera and the light source increase in size, and at the time of installation, those are restricted in size, which has been problematic. In contrast, in the image inspection apparatus according to the present embodiment, the imaging section and the illumination section can be made to be separate members, to allow more flexible installation in view of an arrangement space, which is also an advantage in terms of usability.

(Basic Principle of the Photometric Stereo Method)

Figure 13A:
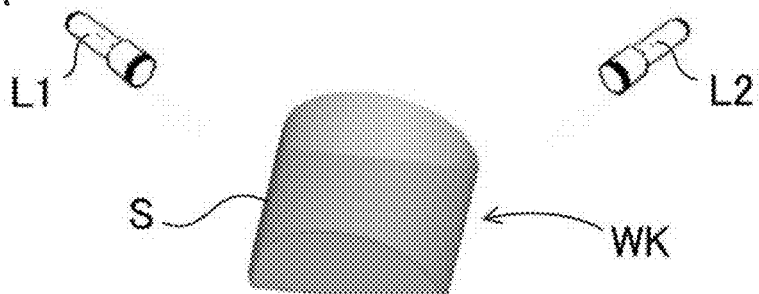
FIG. 13A is a view showing a positional relation between a diffusing reflective surface S and illumination.
Figure 13B:
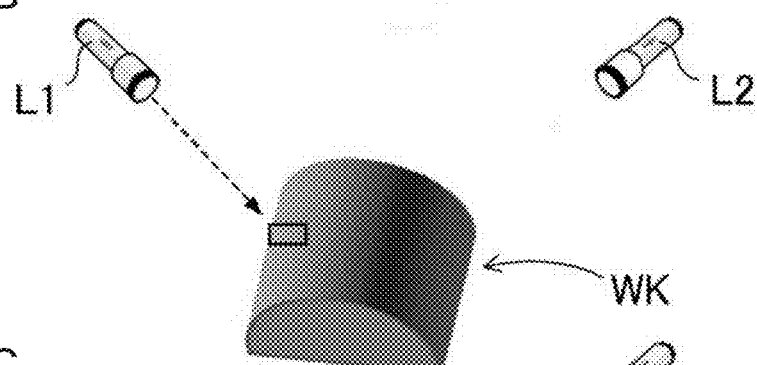
FIG. 13B is a view showing a state where irradiation is performed with light from L1.

Here, the basic principle of the photometric stereo method will be described with reference to FIGS. 13A to 13D. First, as shown in FIG. 13A, there is assumed a case where an unknown diffusing reflective surface S and a plurality of illuminations whose brightness and positions are known (in this example, two illuminations: a first illumination section L1 and a second illumination section L2) are present. For example, as shown in FIG. 13B, when irradiation is performed with light from the first illumination section L1, diffusing reflective light on the surface of the diffusing reflective surface S is decided only by: (1) brightness of the illumination (known); (2) an orientation of the illumination (known); (3) an orientation of the surface of the workpiece WK (normal vector n); and (4) a parameter of an albedo of the surface of the workpiece WK.

Figure 13C:
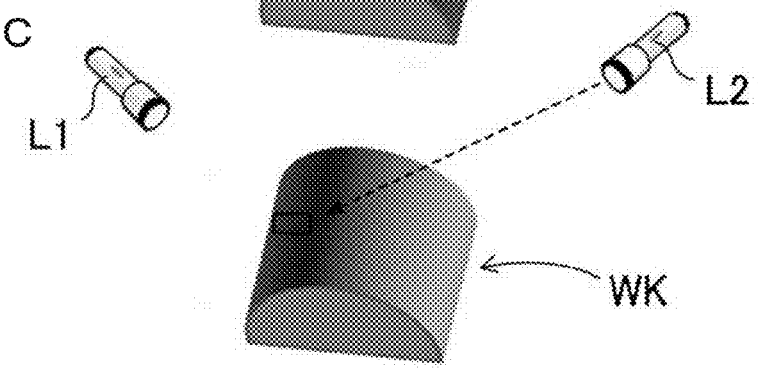
FIG. 13C is a view showing a state where light has been applied from L2.
Figure 13D:
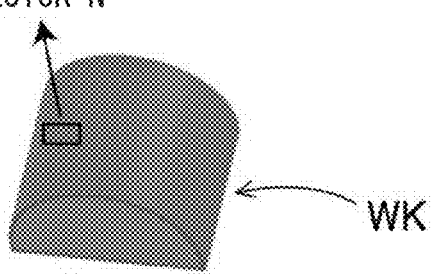
FIG. 13D is a view for explaining that an orientation of the surface is estimated from combination of an irradiation direction and brightness of reflective light, each for explaining a basic principle of a photometric stereo method.

Therefore, as shown in FIG. 13B and FIG. 13C, each of partial illumination images, obtained from diffusing reflective light at the time of projection of illumination light from a plurality of different illumination directions, specifically three or more illumination directions, is captured by the imaging section. Then, as shown in FIG. 13D, three or more partial illumination images are employed as input images, thereby allowing calculation of: (3) an orientation of the surface of the workpiece WK (normal vector n); and (4) an albedo of the surface of the workpiece WK, which are unknown, from the following relational expression.

$$I = \rho L S n$$

where $\rho$ is an albedo, L is brightness of the illumination, S is a matrix in the illumination direction, n is a normal vector of the surface, and I is a tone value of the image.

From the above expression, when the number of illumination sections is three, the following expression is given.

$$\begin{pmatrix} I_1 \\ I_2 \\ I_3 \end{pmatrix} = \rho L \begin{pmatrix} s_{11} & s_{12} & s_{13} \\ s_{21} & s_{22} & s_{23} \\ s_{31} & s_{32} & s_{33} \end{pmatrix} \begin{pmatrix} n_x \\ n_y \\ n_z \end{pmatrix} \quad \text{[Mathematical Expression 1]}$$

Further, when the number of illumination sections is four, the following expression is given.

$$\begin{pmatrix} I_1 \\ I_2 \\ I_3 \\ I_4 \end{pmatrix} = \rho L \begin{pmatrix} s_{11} & s_{12} & s_{13} \\ s_{21} & s_{22} & s_{23} \\ s_{31} & s_{32} & s_{33} \\ s_{41} & s_{42} & s_{43} \end{pmatrix} \begin{pmatrix} n_x \\ n_y \\ n_z \end{pmatrix} \quad \text{[Mathematical Expression 2]}$$

(Normal Vector n)

From the above expression, the normal vector n can be expressed by the following expression.

$$n = 1/\rho L \cdot S^{+} I$$

In the above expression, when "$S^{+}$: a square matrix", "a normal inverse matrix $S^{+}$: an inverse matrix of a longitudinal matrix" is found by Moore-Penrose pseudo-inverse matrix $S^{+} = (S'S)^{-1} S^{t}$.

(Albedo)

Further, the albedo $\rho$ can be expressed by the following expression:

$$\rho = |I|/|LSn|$$

(2-2. Contour Extraction Image)

Next, a description will be given of a method for generating an inclination image by the photometric stereo method and obtaining information of the surface of the workpiece, such as a flaw and a contour, from the obtained inclination image.

(Inclination Image)

First, a method for generating the inclination image will be described. When it is assumed that the curved surface of the workpiece is S, the inclination image is given by the following expression:

$$X\text{-direction: } \delta s/\delta x, \quad Y\text{-direction: } \delta s/\delta y$$

Figure 14A:
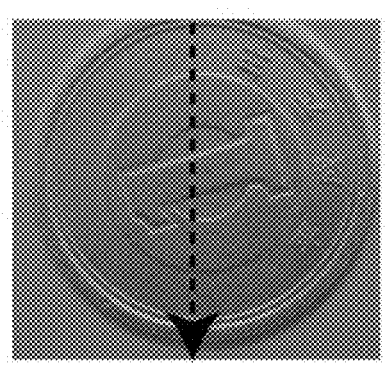
FIG. 14A is a view showing one example of a Y-coordinate component image in a normal direction.
Figure 14B:
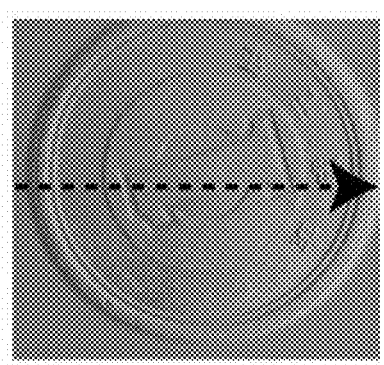
FIG. 14B is a view showing one example of an X-coordinate component image in the normal direction.

Here, as examples of the inclination image, FIGS. 14A and 14B show examples of using a one-yen coin as the workpiece. FIG. 14A is a Y-coordinate component image in a normal direction, and FIG. 14B is an X-coordinate component image in a normal direction. Here, by use of partial illumination images captured from four illumination directions, an inclination image shown in FIG. 14A is obtained by performing differentiation in the Y-direction (a vertical direction in the drawing), and an inclination image shown in FIG. 14B is obtained by performing differentiation in the X-direction (a horizontal direction in the drawing).

Here, since a flaw, a contour and the like are places where the inclination of the surface of the work piece changes, the inclination images are differentiated in the respective directions. The secondary inclination image is given by the following expression:

$$X\text{-direction: } \delta^2 s/\delta x^2, \quad Y\text{-direction: } \delta^2 s/\delta y^2$$

(Contour Extraction Image)

Thus, the portions $\delta^2 s/\delta x^2$, $\delta^2 s/\delta y^2$ of the inclination images in the X-direction and the Y-direction are synthesized to generate a contour extraction image including information of a contour and a flaw of the workpiece. A contour extraction image E is given by the following expression.

$$E=\delta^2 s/\delta x^2+\delta^2 s/\delta y^2$$

Figure 14C:
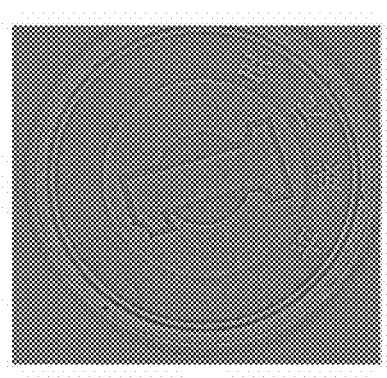
FIG. 14C is a view showing one example of a contour extraction image.

In the above expression, E represents contour information, and S represents the curved surface of the workpiece. FIG. 14C shows an example of the contour extraction image computed from FIGS. 14A and 14B. In the contour extraction image, a height is expressed by gradation (luminance) of the image such that a high portion is colored in white and a low portion is colored in black.
(Differentiation Synthesis Method)

Examples of a differentiation synthesis method that is performed in generating the contour extraction image include: (1) simple addition; (2) multiple resolution; and (3) square sum.
(1. Simple Addition)

Here, "(1) simple addition" is a sum of differentials of X/Y-inclination images at each pixel.
(2: Double Resolution)

Further, "(2) multi-resolution" is obtained by creating a plurality of reduced inclination images, obtained by reducing the inclination image at different reduction ratios, and finding intensity of a contour in each of the reduced inclination images by the method of (1). The reduction ratios are, for example, 1/1, 1/2, 1/4, 1/8, 1/16, 1/32 and the like. The plurality of reduced contour images as thus obtained are subjected to predetermined weighting and enlargement processing, and an image obtained by adding all the enlarged reduced contour images is regarded as a contour extraction image. Here, when the weighting is changed, a flaw, a contour and the like each having an arbitrary thickness can be extracted.
(3. Square Sum)

Further, in "(3) square sum", a contour extraction image is created in which a sum of a square of differentials of the X/Y-inclination images is regarded as intensity of a contour. It is to be noted that "(2) multi-resolution" is adopted in the present embodiment.

A size used for flaw determination varies depending on the user's use. For example, a depression over ten pixels may be determined as a flaw, or a depression over 100 pixels may be determined as a flaw. Further, only a steep edge may be to be extracted as an edge.

When the number of pixels of the inclination image is large, it is regarded as a large flaw in the processing. Therefore, when a large flaw is to be extracted, an inclination image is reduced, intensity of a contour is found by the method of (1), and then the image is enlarged. On the other hand, when a small flaw is to be extracted, differential synthesis may be performed by the method of (1) without performing weighting.

That is, in the weighting, a previously decided weighting set is prepared at the time of synthesis, and reduced inclination images of all the kinds described above are created. Then, when a large flaw is to be seen, a result from the more reduced image is weighted, and when a small flaw is to be seen, a result from the less reduced image is weighted.

Here, the contour extraction image is obtained by adding all the reduced contour images having been enlarged. Since a flaw is normally detected over a plurality of frequencies, when the frequency is limited to one frequency, for example, only a flaw detected at that limited frequency is extracted and hence the image blurs as a whole.

(Characteristic Size)

The foregoing weighting set is formed such that, for example, a parameter named a "characteristic size" is provided, the thinnest flaw can be detected when this value is 1, and a larger flaw is detected as this value continues to be increased. When the characteristic size continues to be increased and the image comes into a state where a larger flaw is easy to detect, the roughness of the surface of the workpiece becomes more apparent. Therefore, a predetermined threshold may be provided for the characteristic size, and a case where the characteristic size is equal to or larger than the threshold is a roughness mode, which may then be used separately from a contour extraction mode, depending on the characteristic size of the contour extraction image.

Next, a method for calculating $\delta^2 s/\delta x^2$ and $\delta^2 s/\delta y^2$ will be described. Examples of this calculation method include: (1) forward difference; and (2) central difference.
(1. Forward Difference)

In the forward difference, an inclination image Gh in the horizontal direction and an inclination image Gv in the vertical direction are regarded as input, and a pixel G(x, y) at coordinates (x, y) of a contour image E is calculated by the following expression:

$$E(x,y)=Gh(x-1,y)-Gh(x,y)+Gv(x,y-1)-Gv(x,y)$$

Figure 15A:
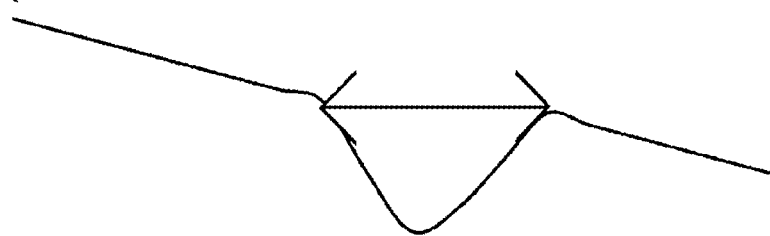
FIG. 15A is a view showing surface information.
Figure 15B:
FIG. 15B is a diagram showing an inclination image.
Figure 15C:
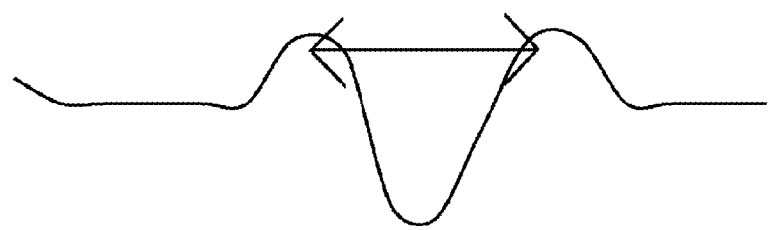
FIG. 15C is a view showing a forward difference.
Figure 15D:
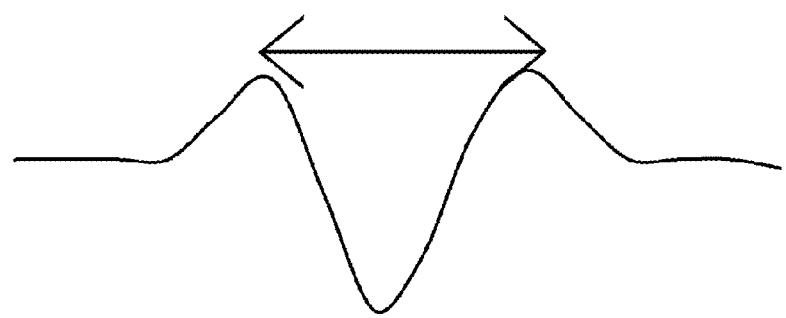
FIG. 15D is a view showing a central difference, each for explaining a method for calculating $\delta^2 s/\delta x^2$ and $\delta^2 s/\delta y^2$.

Here, FIGS. 15A to 15D show information of a flaw that appears in a contour image as schematic profiles. In these drawings, FIG. 15A shows a profile of surface information of the workpiece, FIG. 15B shows a profile of an inclination image, FIG. 15C shows a profile of a contour image by means of a forward difference, and FIG. 15D shows a profile of the contour image by a central difference. As shown in FIGS. 15A and 15C, "(1) forward difference" has an advantage in that a flaw in units of one pixel can be clearly seen, but has a disadvantage in that an image displaced by 0.5 pixels from the original image is obtained.
(2. Central Difference)

Next, a method for calculating $\delta^2 s/\delta x^2$ and $\delta^2 s/\delta y^2$ by means of the central difference will be described. An inclination image Gh in the horizontal direction and an inclination image Gv in the vertical direction are regarded as input, and a pixel G(x, y) at coordinates (x, y) of a contour image E is calculated by the following expression:

$$E(x,y)=Gh(x-1,y)-Gh(x+1,y)+Gv(x,y-1)-Gv(x,y+1)$$

As shown in FIGS. 15A and 15D, "(2) central difference" has an advantage in that coordinates are not displaced from the original image, but has a disadvantage in that a result slightly blurs.
(2-3. Texture Extraction Image)

Next, a description will be given of a method for removing the surface state of the workpiece from an inclination image obtained by the photometric stereo method, to obtain a texture extraction image preferable for detection of a character, and the like. First, texture information is calculated from the albedo ρ of the surface of the workpiece. The albedo ρ is given by the following expression.

$$\rho=|I|/|LSn|$$

where ρ is an albedo, L is brightness of the illumination, S is a matrix in the illumination direction, n is a normal vector of the surface, and I is a tone value of the image.

It is to be noted that, while it is possible to find one texture extraction image (albedo) by the expression: ρ=|I|/|LSn|, it is also possible to find N texture extraction images (albedos) from a normal vector obtained by this expression and N input images (partial illumination images) and synthesize the texture extraction images, so as to find one texture extraction image (albedo). Examples of a specific synthesis method include an average method and a halation removing method.

Figure 16A:
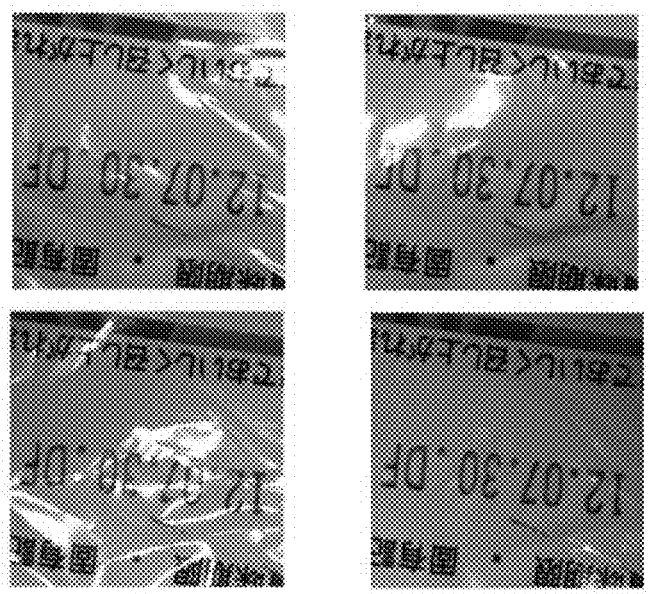
FIG. 16A is a view showing a source image.
Figure 16B:
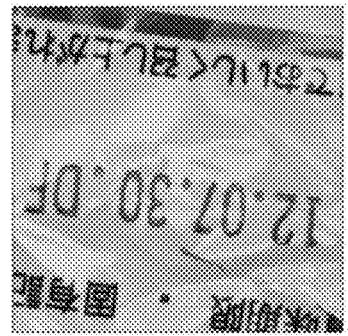
FIG. 16B is a view showing an image subjected to processing by an average method.
Figure 16C:
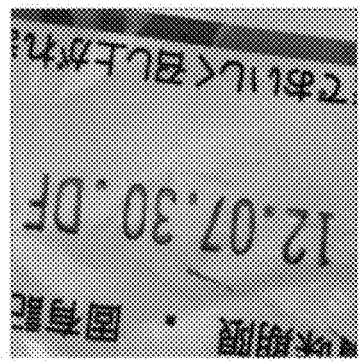
FIG. 16C is a view showing an image subjected to processing by a halation removing method, each for explaining a method for generating a texture extraction image.

FIGS. 16A to 16C show examples of the texture extraction image. In these drawings, FIG. 16A shows four texture extraction images as input images, FIG. 16B shows a texture extraction image obtained by applying the average method to these images, and FIG. 16C shows a texture extraction image obtained by applying the halation removing method to these images.

(1: Average Method)

The average method is a method where at each pixel, an average value of N albedos ρ is regarded as a pixel value of that pixel. As shown in FIG. 16B, although the shadow is entirely erased, the shadow in a portion where halation has occurred in the input image cannot be erased by the photometric stereo method, and hence an image where an influence of the halation remains is obtained. That is, in the four input images (partial illumination images) of FIG. 16A, white places are places where halation has occurred. When averaging is performed by the average method, as shown in FIG. 16B, the roughness is removed to a certain extent and the image becomes easier to read, but the roughness slightly remains on a base.

(2: Halation Removing Method)

The expression: ρ=|I|/|LSn| itself exceeds its application range due to a limitation on a dynamic range of the camera as the imaging section and the diversity of reflectivity of the surface of the workpiece, and hence p includes an error. In order to correct this error, the halation removing method can be used.

Since a place where halation occurs is decided by a position of illumination, it is considered that basically, halation does not occur in the same place in the four partial illumination images. Specifically, although halation may occur over two places between two directions, it can be said that halation basically does not occur in the same place unless two illuminations are used.

In the halation removing method, at the time of synthesizing a illumination-direction-specific texture extraction image calculated from N partial illumination images, considering that there is much halation in a partial illumination image with the largest pixel value at each pixel or in partial illumination images with the largest to N-th largest pixel values, those are removed and the synthesis is then performed.

Specifically, when each of pixels of the four illumination-direction-specific texture extraction images in the present embodiment is synthesized with, the third largest pixel value (e.g. albedo value or luminance), an image as shown in FIG. 16C is obtained, and an influence of halation can be removed. It is to be noted that, when the fourth largest pixel value is adopted, a slightly dark image is obtained due to an influence of a shadow. On the contrary, when the second largest pixel value is adopted, the influence of halation slightly remains.

Further, in the case of the illumination sections being in the eight directions, the fifth largest pixel value is adopted on the assumption that the influence of halation is not exerted on the fifth largest pixel value or the following pixel value. According to a test performed by the inventor, it has actually been confirmed that the best image is obtained when the fifth largest pixel value is adopted. Further, it has also been proved that the influence of the shadow is exerted when the sixth largest pixel value or the following pixel value is adopted.

It is to be noted that the synthesis method and the averaging are not restricted to these, and a variety of methods can be used. For example, the foregoing halation removing method and average method may be combined, to sort albedo values and adopt values in a specific orders from the top. For example, the third and fourth values may be averaged.

(Characteristic Size)

Next, a detail of the setting will be described. As described above, at the time of creating the contour extraction image, the characteristic size can be set. By setting the characteristic size to not smaller than a predetermined value, a contour extraction image suitable for OCR can be obtained.

(3-2. Gain)

At the time of creating a contour extraction image or a texture extraction image, in the process of generating each of these images, it is possible to multiple a pixel value of the original image by a gain.

The gain at the time of creating a contour extraction image refers to a constant at the time of dispersing a pixel value calculated by calculation processing to a gradation of 0 to 255. For example, when a flaw, a contour or the like is so shallow that it is difficult to grasp the flaw, the contour or the like, a change in gradation of the pixel value increases by increasing this gain value, and hence the flaw, the contour or the like becomes easy to grasp.

Further, the flaw, the contour or the like becomes easy to grasp by performing adjustment such that, when the pixel value calculated by the calculation processing exceeds the range of 0 to 255, it is made to be within that range, and when the pixel value is smaller than the range of 0 to 255, it is extended into that range.

In the foregoing halation removing method, since albedo values are sorted and, for example, the third value from the top is adopted, the brightness of the generated image cannot be expected. Accordingly, as a result of removal of regular reflection, the image may become dark contrary to the expectation. Therefore, in order to adjust the brightness, the pixel value is multiplied by a predetermined gain at the time of creating a texture extraction image.

It is to be noted that, also at the time of calculating an inclination image, adjustment can be performed by means of a gain such that the pixel value is made to be within the range of 0 to 255.

(3-3. Noise Removing Filter)

At the time of creating an inclination image or the like, calculation is to be performed by a set of simultaneous equations by use of a plurality of images, but in practice, differential calculation is performed. Here, noise exists in image data which is obtained by imaging by the imaging section, when the image data is raw data. Therefore, a noise component may be emphasized and a contour may become rough at the time of creating an inclination image. In order to reduce such noise, a noise removing filter such as a guided filter is used. A general low-pass filter may hide or remove not only noise but information of a flaw. On the contrary, a guided filter can remove noise while keeping an edge at the time of finding the inclination image, which is preferable.

(3-4. Angle-Noise Reduction)

Figure 17:
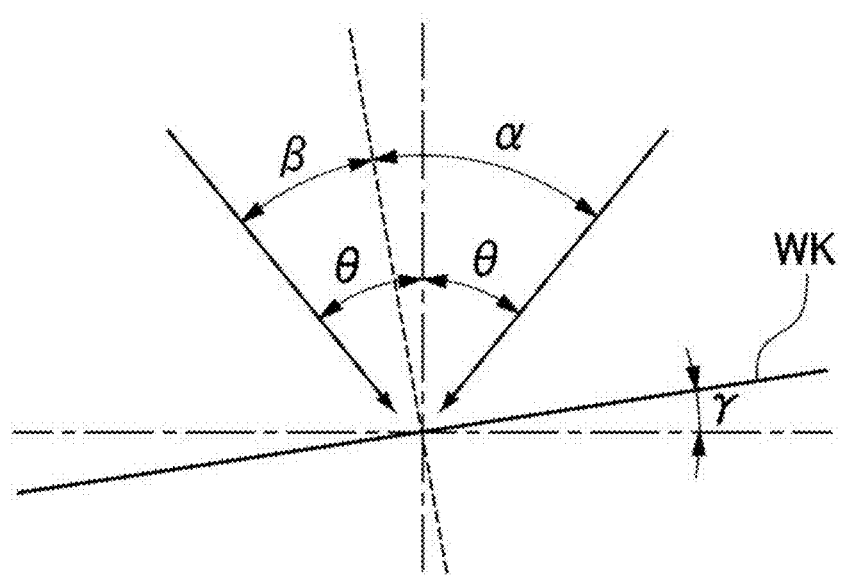
FIG. 17 is a diagram for use in explaining angle-noise reduction.
Figure 18A:
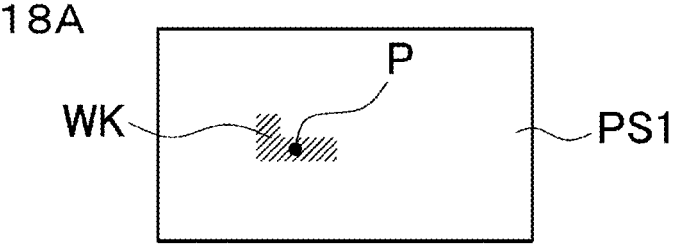
FIGS. 18A to 18D are schematic plan views showing PS1 to PS4 images in the case of the workpiece being a moving body that moves at a uniform speed.
Figure 18B:
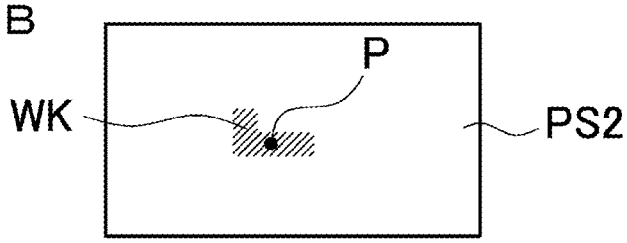
Figure 18C:
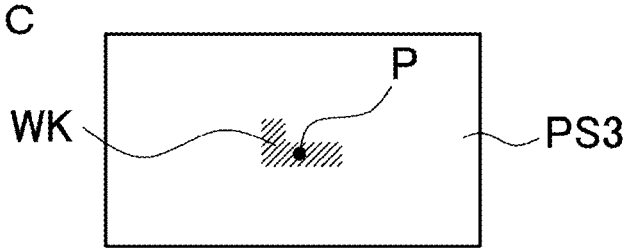
Figure 18D:
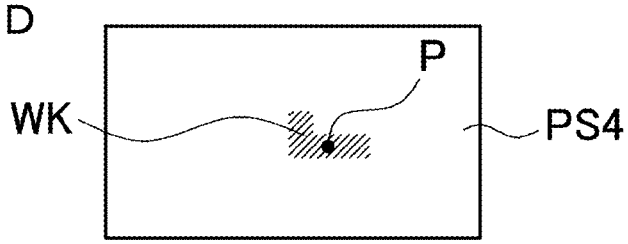

Next, a principle of angle-noise reduction will be described with reference to a schematic view of FIG. 17. As shown in this drawing, there are two illuminations whose incident angles are α and β. When the workpiece WK is assumed to be formed of the diffusing reflective surface and setting is performed such that the inclination of the workpiece WK with respect to the reference plane is γ, an angle between a line perpendicular to the reference plane and an incident is θ, the brightness of reflective light from the illumination α is $I_\alpha$ and the brightness of reflective light from the illumination is $I_\beta$, γ is given by the following expression:

$$\gamma = \arctan(A \cdot |I_\beta - I_\alpha|/|I_\beta + I_\alpha|), A = \cot\theta$$

Angle-noise reduction is to forcibly make the inclination γ be 0 when $|I_\beta + I_\alpha|$ is small to a certain extent.

When it is assumed that both $I_\beta$ and $I_\alpha$ are extremely dark and $I_\beta=2$ and $I_\alpha=1$, for example, $|I_\beta-I_\alpha|/|I_\beta+I_\alpha|$ becomes a value as large as ⅓. On the other hand when it is assumed that both $I_\beta$ and $I_\alpha$ are bright and $I_\beta=300$ and $I_\alpha=200$, for example, $|I_\beta-I_\alpha|/|I_\beta+I_\alpha|$ becomes a value as small as ⅕. $I_\beta=2$ and $I_\alpha=1$ greatly affects inclination although there is simply a possibility of noise. Thus, in order to reduce an influence of such noise, the angle-noise reduction is applied to allow setting of a threshold of $|I_\beta+I_\alpha|$ for forcibly making the inclination be 0.

(Image Inspection on Moving Workpiece)

The image inspection by the photometric stereo method is performed on the assumption that image processing is performed on partial illumination images PS1, PS2, PS3, . . . , which are captured by illuminating the same workpiece from three or more different illumination directions. In other words, an ordinary photometric stereo method is performed on the assumption that a subject is still and the position of each of the plurality of captured images is the same as that of the subject. For this reason, when the workpiece moves, since imaging timing for capturing each partial illumination image is different, the workpiece moves between the imaging timing, resulting in that the position of each of the images is not the same as that of the workpiece, and the photometric stereo method cannot be applied if this state remains. For example, in the case of capturing four partial illumination images of a workpiece being carried on a line for performing photometric stereo processing, as shown in FIG. 18, even with an imaging interval of as short as 4 ms, the workpiece moves on the order of several to several hundreds of pixels while four partial illumination images PS1 to PS4 are captured. This results in differences in coordinates of a corresponding position P of the workpiece WK among each of the images PS1 to PS4.

Therefore, it is necessary to perform a registration operation for registering a corresponding relation among the partial illumination images each captured at different imaging timing so as to match corresponding points of the images. As a method for implementing registration of images, an optical flow-based method is considered. In this method, a portion suitable for tracking is automatically selected from a target image, and in order to track that portion, a similarity degree or a difference degree such as ZNCC (Zero-mean Normalized Cross-Correlation), an SAD (Sum of Absolute Difference) or an SSD (Sum of squared difference) is calculated for each of moving position candidates from the tracking target image. With the calculated values, a movement vector is found, to calculate geometric transformation required for the registration. Further, there is also considered a model-based method where a model is created in advance from an image of the workpiece and geometric data which are suitable for tracking, and tracking is then implemented by use of that model.

However, since it is assumed in either of these methods that an illumination state does not greatly change, it has been difficult to implement stable registration between images in which the illumination states greatly change, such as images captured by the photometric stereo method.

Therefore, in the present embodiment, in order to realize image inspection also on a moving workpiece by the photometric stereo method, the following configuration has been adopted. A tracking target image is set in advance, a plurality of reference images, each captured by simultaneously turning on a plurality of illumination sections, are captured before and after, or in the middle of capturing of a series of partial illumination images at different timing, a position including the tracking target image is estimated in each of the reference images by the corresponding relation estimating section, and with the estimated position, a corresponding relation of corresponding pixels in each of the partial illumination images is estimated, to generate an inspection image by the photometric stereo method by the inspection image generating section. This has allowed inspection of a flaw and a printed character on a moving workpiece.

In addition, it is also possible to include, in the information of the position of the tracking target image estimated by the corresponding relation estimating section, information of a rotational angle (attitude) in addition to a coordinate position at which the tracking target image exists in the first reference image or the second reference image.

(4. Image Registration Section)

An image registration section is, for example, configured of the image processing part 41 in the example of FIG. 1, and processed by software. Here, an operation of the imaging registration section will be described.

In the case of the workpiece moving, the workpiece moves while partial illumination images are being captured, and hence a position of a pixel corresponding to the workpiece differs in each of the partial illumination images. Therefore, as a method for generating an inspection target image from the partial illumination images obtained by capturing the moving workpiece by the photometric stereo method, there are considered: (1) approach (referred to as "linear interpolation approach") where a reference image is created and an image that matches with the reference image is extracted by linear interpolation to establish image registration and acquire an illumination direction from position information of the extracted image; and (2) approach (referred to as "model image approach") where a model image with a changed illumination direction is created in advance and an image that matches with a model image group registered in association with the illumination direction is extracted, to establish image registration and acquire an associated illumination direction from the matched model image.

First, in "(1) linear interpolation approach", a region to be searched is narrowed by linear interpolation. Accordingly, when "(2) model image approach" is applied to the narrowed region, even in a case where complete matching is not realized by the linear interpolation due to position displacement or angle displacement, it is possible to solve such a problem of position displacement and the like. That is, by applying displacement correction, the image registration can be realized with higher accuracy. That is, when "(1) linear interpolation approach" is regarded as a main approach and "(2) model image approach" is regarded as a preliminary approach, "(2) model image approach" is performed for the displacement correction.

At the time of creating a model image in "(2) model image approach", examples of a method include: (A) PS model method where an actually captured image is regarded as a model image; and (B) virtual model method where a virtually created image is regarded as a model image.

In the present embodiment, it is possible to realize establishment of the image registration from "(1) linear interpolation approach", with the "(2) model image approach" performed for the displacement correction. Hereinafter respective examples of (1) and (2) will be described.

(4-1. Explanation of Terms)

First, since abbreviations is used in the description, meanings of the abbreviations are clarified. PS is an abbreviation of Photometric Stereo, and photometric stereo processing is referred to as PS processing. A partial illumination image obtained by imaging by turning on one of a plurality of illumination sections for the photometric stereo processing is referred to as a PS image, and an operation of capturing the PS image is referred to as PS imaging. Further, in this embodiment, four illumination sections of the first illumination section 21, the second illumination section 22, the third illumination section 23 and the fourth illumination section 24 are used, and in the meaning of imaging, images or processing for the PS processing by the first to fourth illumination, PS1, PS2, PS3 and PS4 are numbered. That is, it does not necessarily mean that an image captured by the first illumination section 21 is PS1, an image captured by the second illumination section 22 is PS2, and so on. A corresponding relation between the PS image and the illumination section is arbitrarily decided in accordance with a mode of installation of the illumination section or the turning-on order of the illumination section. For example, the turning-on order in which the illumination controlling section switches turning-on of each of the illumination sections can be clockwise, counterclockwise, or random. However, in the following description, for the sake of simplification, a description will be given assuming that imaging is performed clockwise in the order of the first illumination section 21, the second illumination section 22, the third illumination section 23 and the fourth illumination section 24, and obtained partial illumination images are numbered as PS1, PS2, PS3 and PS4. It is to be noted that in the case of adding an asterisk *, it means "arbitrary". For example, in the case of referring to a PS* image, it means an arbitrary PS image.

MC is an abbreviation of Motion Correction. As shown in FIG. 19A, processing of turning on all of the first illumination section 21 to the fourth illumination section 24 before and after, or in the middle of the PS imaging and performing imaging for linear interpolation is referred to as MC imaging. An image obtained by the MC imaging is referred to as an entirely turning-on image (MC image). An example of FIG. 19A shows the timing for sequentially capturing MC1, PS1, PS2, PS3, PS4, MC2, PS1', PS2', PS3', PS4', MC3, . . . images by an interpolation-linear interpolation method (detailed later). There are a plurality of MC images, however, a first entirely turning-on image MC1 and a second entirely turning-on image MC2 are mainly used in the following description. In the example of FIG. 19A, the first entirely turning-on image MC1 means an image at the time of entirely turning-on illumination before the PS imaging, and the second entirely turning-on image MC2 means an image at the time of entirely turning-on illumination after the PS imaging. MC* means processing either before or after, or both before and after the PS imaging. However, the timing for capturing the first entirely turning-on image MC1 and the second entirely turning-on image MC2 is not restricted to the example of FIG. 19A, and for example in the case of an extrapolation-linear interpolation (detailed later), as shown in FIG. 19B, imaging is performed in the order of MC1, MC2, PS1, PS2, PS3 and PS4. Further, although an example of using two MC images is shown in the foregoing example, the present invention is not restricted to this, and the number of MC images for interpolation can be increased to three or more. As one example, FIG. 19C shows imaging timing for each image in the cases of the number of MC images being two, three and five. In these drawings, C and D show the imaging timing in the case of setting the number of MC images to two as shown in FIG. 19A and FIG. 19B, respectively. Further, E and F show a modified example of the imaging timing in the case of setting the number of MC images to three, and G shows an example of the imaging timing in the case of setting the number of MC images to five. As thus described, the number of captured MC images and the imaging timing are selected as appropriate in accordance with the required accuracy, the complex of movement of the workpiece, the interpolation method to be used, or the like.

XYT is an abbreviation of a position (x, y) and an angle $\theta$ (theta), and means a position and an attitude in an image.

DOF is an abbreviation of Degree of Freedom, and means a degree of freedom. For example, when there are six degrees of freedom: parallel movement X, parallel movement Y, rotation, scale, aspect and skew, those are represented as DOF=6.

SW is an abbreviation of Search Window, and means a search region in the MC* image, which is a region for calculating a similarity degree (or difference degree) between images to define a range for searching the most similar image. In the following description, SW1 and SW2 are mainly used. SW1 is a search region in the MC1 image, and SW2 is a search region in the MC2 image.

TW is an abbreviation of Tracking Window, and means a tracking region for use in a tracking region designating method.

Further, PW is an abbreviation of Pattern Window, and means a pattern region for use in a tracking pattern designating method. Both the tracking region TW and the pattern region PW are regions for designating an image (tracking target image) which tracks a position of the workpiece. Further, the tracking region TW and the pattern region PW are designated by the tracking target image specifying section. Specifically, the tracking region TW designates, at the time of setting of the tracking region designating method, a region including an image that becomes a tracking target at the time of use of the method (cf. FIGS. 20, 21A and 22F, described later). At the time of use of the tracking region designating method, a search is performed from the first reference image and the second reference image by means of the entire region designated by the tracking region TW.

It is to be noted that the tracking target image is not necessarily required to be an image of the workpiece WK, and the position of the workpiece WK may be estimated from the position of the tracking target image.

Similarly, the pattern region PW designates, at the time of setting of the tracking pattern designating method, a region including an image that becomes a tracking target at the time of use of the method (cf. FIGS. 23A and 23F, described later). At the time of use of the tracking pattern designating method, an image is extracted by use of the pattern region at the time of setting, and a search is performed from the first reference image and the second reference image by means of the extracted image.

It is to be noted that the tracking target image is typically an image including the whole or part of the workpiece. However, the present invention does not restrict the tracking target image to the image of the workpiece, but an image by which movement of the workpiece can be confirmed may be sufficiently used, and for example, a background image of the workpiece, such as an image of a tray or a conveyer to place the workpiece on can also be used as the tracking target image.

MW is an abbreviation of Measure Window, and means a measurement region, showing a region of a measurement target in a 1D-edge method.

(4-2. Linear Interpolation)

Next, the linear interpolation method for performing linear interpolation will be described. Examples of the linear interpolation method includes: (1) tracking region designating method; (2) tracking pattern designating method; and (3) 1D edge method. Hereinafter, operations at the time of setting and use of each of the methods will be described.

(1) Tracking Region Designating Method

In the tracking region designating method, an MC*/PS* image group is acquired in a state where the workpiece WK is moving similarly to the time of use of the method, or in a state where the workpiece WK is still. A setting is performed while referring to the image group as thus acquired.

(Setting of the Tracking Region Designating Method)

In this tracking region designating method, a tracking region TW to start tracking and a search region SW2 are set at the time of setting. FIGS. 20A and 20B show a state of this setting. As shown in FIG. 20A, the tracking region TW is set with respect to the MC1 image. As shown in FIG. 20B, the search region SW2 is set with respect to the MC2 image. Moreover, it is also possible to set an angle displacement amount assumed from a linear interpolation angle, and set a position displacement amount assumed from a linear interpolation position.

(Use of Tracking Region Designating Method)

Figure 21A:
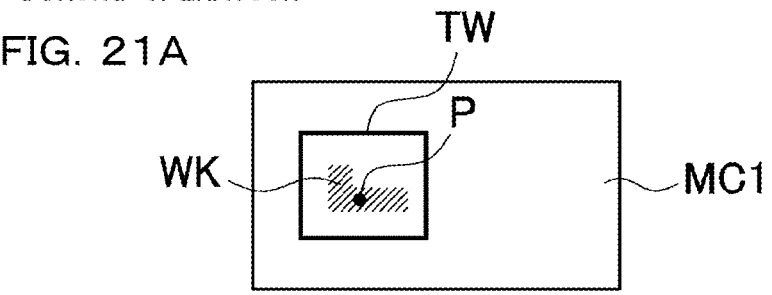
FIG. 21A is a view showing MC1.
Figure 21B:
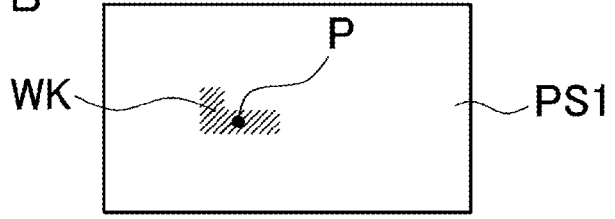
FIG. 21B is a view showing PS1.
Figure 21C:
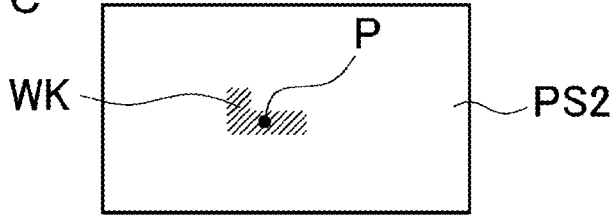
FIG. 21C is a view showing PS2.
Figure 21D:
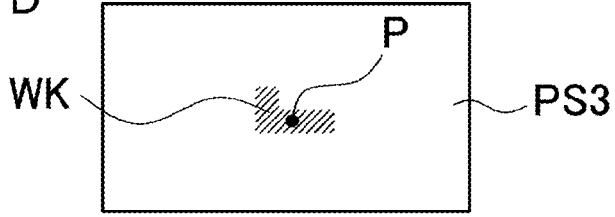
FIG. 21D is view showing PS3.
Figure 21E:
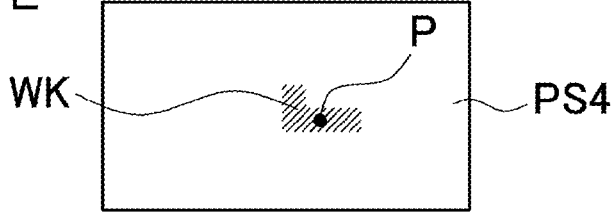
FIG. 21E is view showing PS4.
Figure 21F:
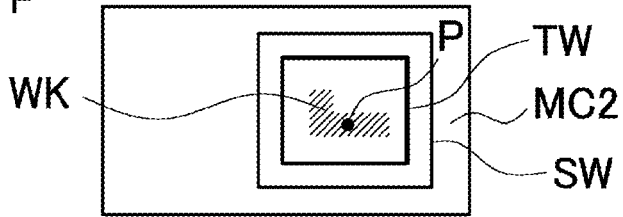
FIG. 21F is view showing MC2, for explaining each processing at the time of use of the tracking region designating method.

In a state where the setting of the tracking region designating method has been made in such a manner, an operation at the time of use of the method will be described with reference to FIGS. 21A to 21F. First, as shown in FIG. 21A, when entry of the workpiece WK as a target into the tracking region TW is detected by a sensor or the like, or by the user's trigger, the MC1 image is started to be captured.

Alternatively, it may be configured such that the image processing apparatus is made capable of switching a detection mode and a PS mode (photometric stereo mode), and the mode is switched to the PS mode when the workpiece is detected in the detection mode. In the detection mode, for example, the image processing part 41 automatically generates a trigger by an internal timer, to capture an image, and by processing with a relatively light load such as area measurement or gradation measurement, entry of the workpiece WK into a FOV (Field of View) is detected. Further, in the PS mode, when movement correction is required, MC1, PS1, PS2, PS3, PS4 and MC2 images are captured, and the PS processing is performed while the movement correction is performed.

Next, as shown in FIGS. 21A to 21F, MC1 to PS1, PS2, PS3, PS4 to MC2 are captured at regular intervals. Then, by means of an image in a region designated by the tracking region TW in the MC1 image, a pattern search is performed in the search region SW2 in the MC2 image in FIG. 21F. As a method for the pattern search, for example, values of ZNCC given by the following mathematical expression are superimposed for calculation, while a position and an attitude in the image defined by the tracking region TW are changed within a range defined by the search region SW2, thereby to allow decision of a similar position and attitude. In addition, a method for using the pattern and an image pyramid of the tracking target image may be applied for speeding-up.

[Mathematical Expression 3]

$$R_{ZNCC} = \frac{MN\sum_{j=0}^{N-1}\sum_{i=0}^{M-1} I(i,j)T(i,j) - \sum_{j=0}^{N-1}\sum_{i=0}^{M-1} I(i,j) \times \sum_{j=0}^{N-1}\sum_{i=0}^{M-1} T(i,j)}{\sqrt{\left(MN\sum_{j=0}^{N-1}\sum_{i=0}^{M-1} I(i,j)^2 - \left(\sum_{j=0}^{N-1}\sum_{i=0}^{M-1} I(i,j)\right)^2\right)\left(MN\sum_{j=0}^{N-1}\sum_{i=0}^{M-1} T(i,j)^2 - \left(\sum_{j=0}^{N-1}\sum_{i=0}^{M-1} T(i,j)\right)^2\right)}}$$

Here, T(i, j) is a luminance value of a template, and I(i, j) is a luminance value of an image. When a width of the template is m pixels and a height thereof is n pixels, coordinates (i, j) are (0, 0) at its upper left (or lower left), and (m−1, n−1) at its lower right (or upper right).

From the position and attitude data as thus obtained, XYT in PS1 to PS4, namely estimated positions and estimated attitude, can be found by applying the linear interpolation method on the assumption that the workpiece WK is moving at a uniform speed and the imaging timing for the imaging section (e.g., shutter interval of the camera) is constant.

(Interpolation-Linear Interpolation Method)

In the case of using the interpolation-linear interpolation method for calculation in the linear interpolation method, it is performed as follows. When M is an image index of the MC2 image, N is an image index of an image to be estimated, XYT in the MC1 image is (X0, Y0, T0), and XYT in the MC2 image is (XM, YM, TM), estimated XYT in each PS(N) image can be found by the following expression.

$XN=X0+N\times(XM-X0)/M$ $YN=Y0+N\times(YM-Y0)/M$ $TN=T0+N\times(TM-T0)/M$

In the above expression, M and N are both indexes that start from 0. In the example shown in FIG. 19A, it is assumed that M=5 and N=1 to 4.

(Extrapolation-Linear Interpolation)

In the case of using the extrapolation-linear interpolation for calculation in the linear interpolation method, it is performed as follows. When M is an image index of the MC2 image, N is an image index of an image to be estimated, XYT in the MC1 image is (X0, Y0, T0), and XYT in the MC2 image is (XM, YM, TM), estimated XYT in each PS(N) image can be found by the following expression.

$$XN=X0+N\times(XM-X0)/M\ YN=Y0+N\times(YM-Y0)/M$$
$$TN=T0+N\times(TM-T0)/M$$

In the above expression, M and N are both indexes that start from 0. In the example shown in FIG. 19B, it is assumed that M=1 and N=2 to 5.

A DOF for finding position displacement and angle displacement is decided from these values of the estimated position and the estimated attitude and the set values of position displacement and angle displacement.

In a case where a position displacement value is a pixel value and an angle displacement value is an angle value, an image in the tracking region TW is rotated around an angle designated by the estimated angle of the tracking region TW in a range of angle displacement, and the rotated TW images are superimposed around the estimated position in a vertically and horizontally extended range just by a value of position displacement, to calculate a similarity degree or a difference degree and find position/angle information in each PS* image. As thus described, limiting the search range allows significant improvement in stability of the pattern search.

Registration of the PS* image is performed using the position/angle information obtained in such a manner. Then, the PS processing is performed using an image group after the registration. Alternatively, the PS processing may be directly performed using the position/angle information and the PS* image.

In either method, as a method for getting access to pixel information, for example, the nearest neighbor interpolation, bilinear interpolation, bi-cubic interpolation, and the like are known, and these methods can be applied.

In the tracking region designating method, there can be obtained an advantage that a model for search is unnecessary, as compared to the tracking pattern designating method described later. Further, there can also be obtained an advantage that tracking can be performed using a workpiece whose design looks random at a glance, such as a casting surface. Moreover, it is possible to narrow an angle range of a rotational search of MC2.

(2) Tracking Pattern Designating Method

The tracking region designating method has been described as one of the linear interpolation methods. Next, the tracking pattern designating method will be described as another linear interpolation method. In the tracking pattern designating method, an MC*/PS* image group is acquired in a state where the workpiece WK is still. This acquired image group is referred to as a registered image group. The registered image group includes a registered MC* image and a registered PS* image. In the tracking pattern designating method, a setting is performed while referring to the registered image group.

(Setting of the Tracking Pattern Designating Method)

Figure 22A:
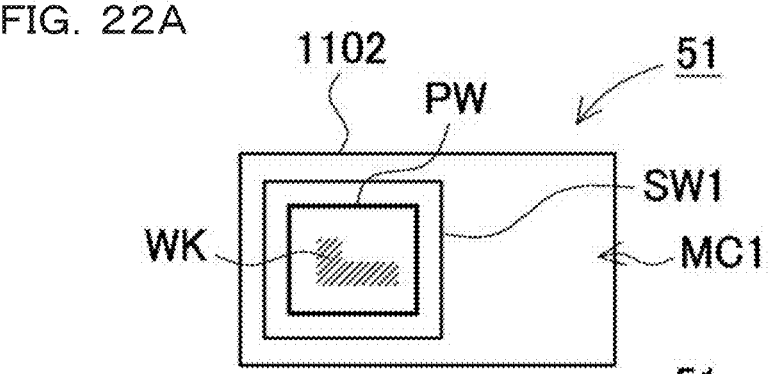
FIG. 22A is a schematic view showing a state where a pattern region PW and a search region SW1 are set on the MC1 image.
Figure 22B:
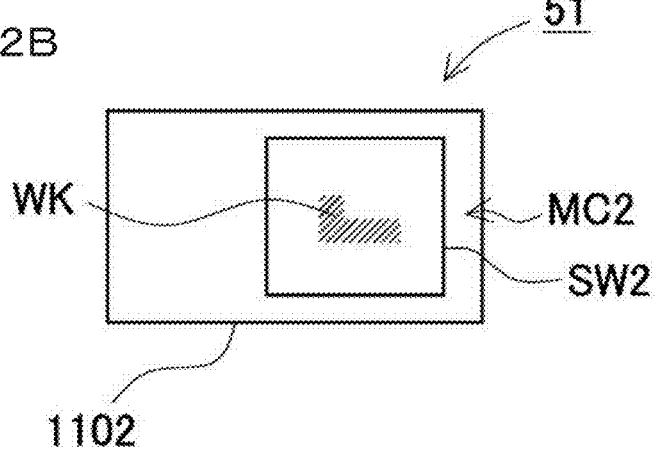
FIG. 22B is a schematic view showing a state where a search region SW2 is set on the MC2 image, at the time of setting of a tracking pattern designating method.

In the setting of the tracking pattern designating method, the pattern region PW, the search region SW1 and the search region SW2, which define a tracking target image (tracking target pattern), are set. FIGS. 22A and 22B show a state of this setting. The pattern region PW and the search region SW1 are set with respect to the MC1 image as shown in FIG. 22A. The search region SW2 is set with respect to the MC2 image as shown in FIG. 22B. The other settings can be made similarly to those of the tracking region designating method described above.

(Use of Tracking Pattern Designating Method)

In a state where the setting of the tracking pattern designating method has been performed in such a manner, an operation at the time of use of the method will be described with reference to FIGS. 23A to 23F. First, as shown in FIG. 23A, when entry of the workpiece as a target into the pattern region PW is detected by the sensor or the like, the MC1 image is started to be captured. Alternatively, similarly to the tracking region designating method, it may be configured such that the detection mode and the PS mode are made switchable, and the mode is switched to the PS mode when the workpiece is detected in the detection mode.

Figure 23A:
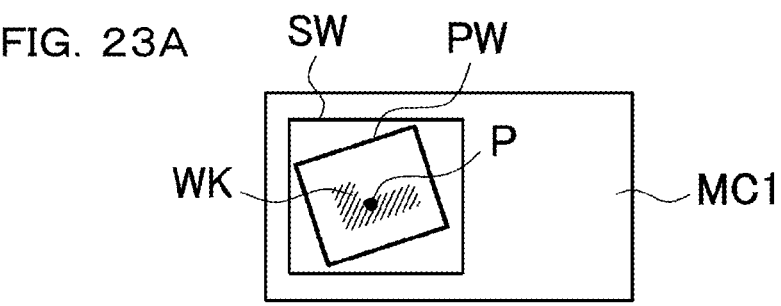
FIG. 23A is view showing MC1.
Figure 23B:
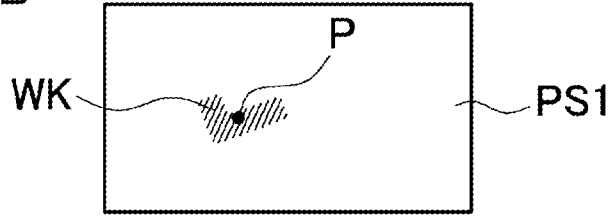
FIG. 23B is view showing PS1.
Figure 23C:
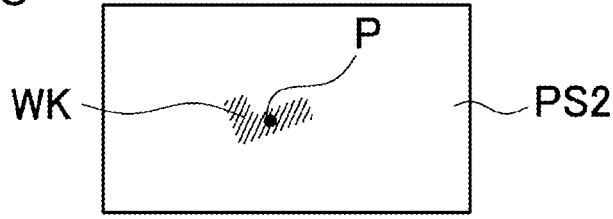
FIG. 23C is view showing PS2.
Figure 23D:
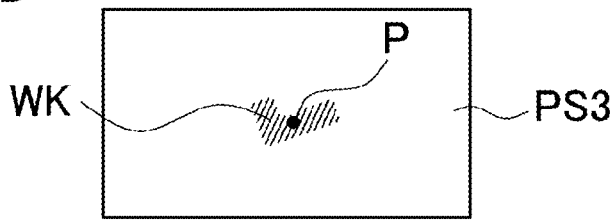
FIG. 23D is view showing PS3.
Figure 23E:
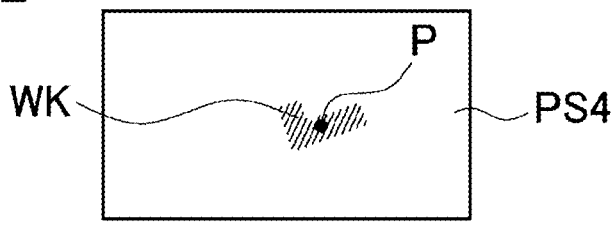
FIG. 23E is view showing PS4.
Figure 23F:
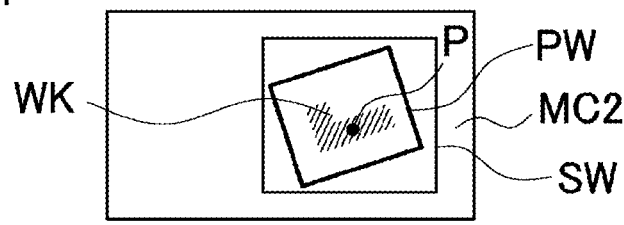
FIG. 23F is view showing MC2, for explaining each processing at the time of use of the tracking pattern designating method.

Next, as shown in FIGS. 23A to 23F, MC1 to PS1, PS2, PS3, PS4 to MC2 are captured at regular intervals. Then, by means of an image (tracking target pattern) in a region designated by the pattern region PW within the registered MC1 image which was set at the time of setting, a search is performed within the search region SW1 of the captured MC1 image. This search includes rotation. Accordingly, as shown in FIG. 23A, a rotated image is detected. This image is employed as a model image for a subsequent pattern search.

Then, the image of MC1 is searched from the search region SW2 in the image of MC2. From XYT information obtained in such a manner, an estimated position in each of the images PS1, PS2, PS3, PS4, namely estimated XYT is found by the linear interpolation. Further, according to the need, it is also possible to decide a window for displacement calculation from the estimated XYT, and perform measurement for displacement calculation within that range.

As a method for the search, for example, values of ZNCC given by Mathematical Expression 3 described above are superimposed for calculation, while a position and an attitude in an image (tracking target pattern) defined by the pattern region PW within the registered MC1 image are changed within a range defined by the search region SW2 within the MC2 image, thereby to allow decision of a similar position and attitude. In addition, similarly to the tracking region designating method, a method for using a template image and an image pyramid of a search image may be applied for speeding-up.

The PS processing can be performed with the position and attitude data as thus obtained, in a similar manner to the tracking region designating method.

The advantages of the tracking region designating method are that a position and an attitude in a model image are made clear after the PS processing; that the accuracy in position of the tracking target is not required to be high; and that the position of the tracking target is limited by a search and thus tracking becomes stable. On the other hand, the disadvantages are: that the processing for creating a model image is required in advance differently from the tracking region designating method; that a memory for a model image is required; and that the first search is a search including rotation in a broad range and thus a processing load increases.

(Image Inspection Program Setting Screen)

Figure 24:
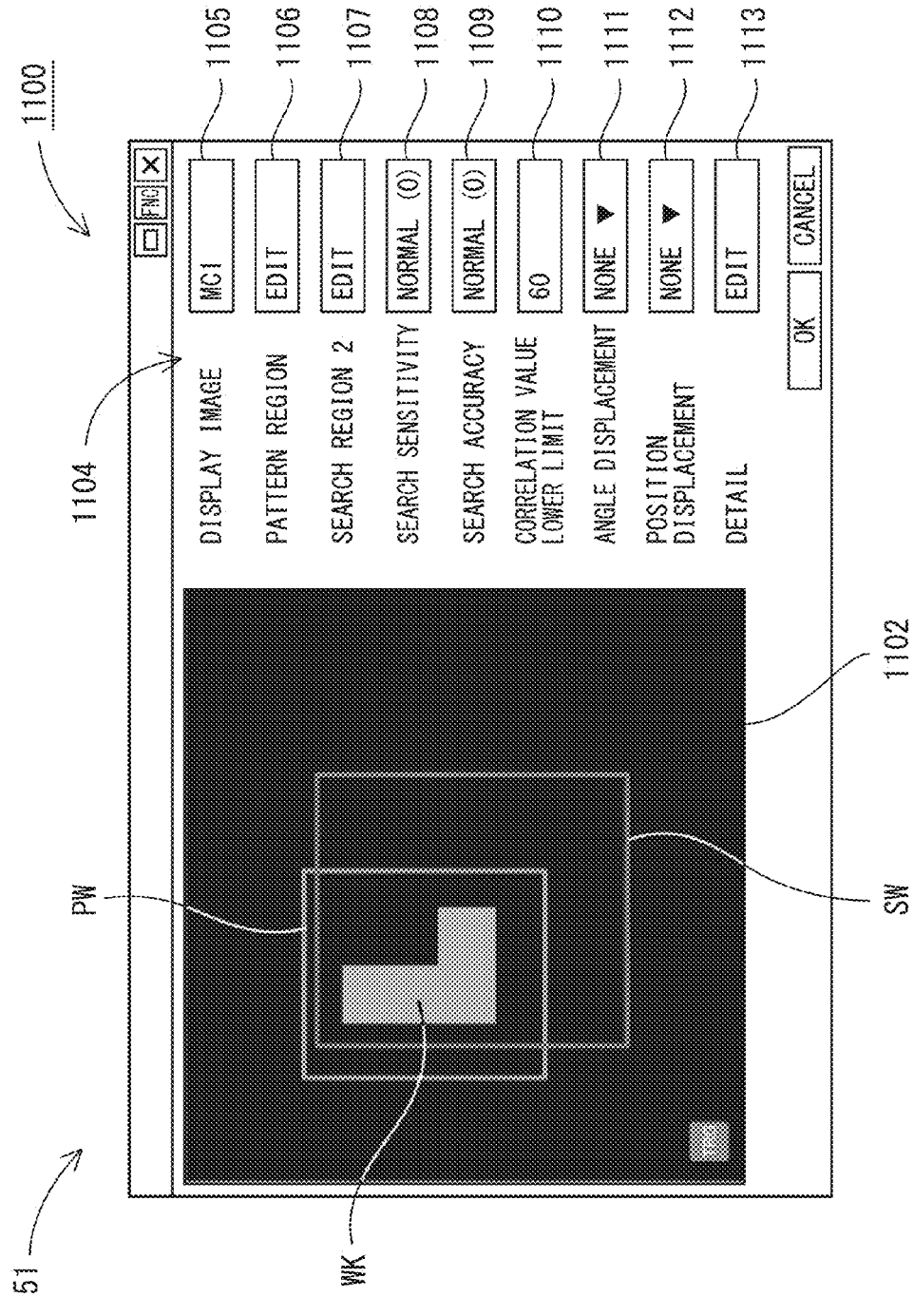
FIG. 24 is a view showing a setting GUI in a GUI mainly for the tracking region designating method.
Figure 25:
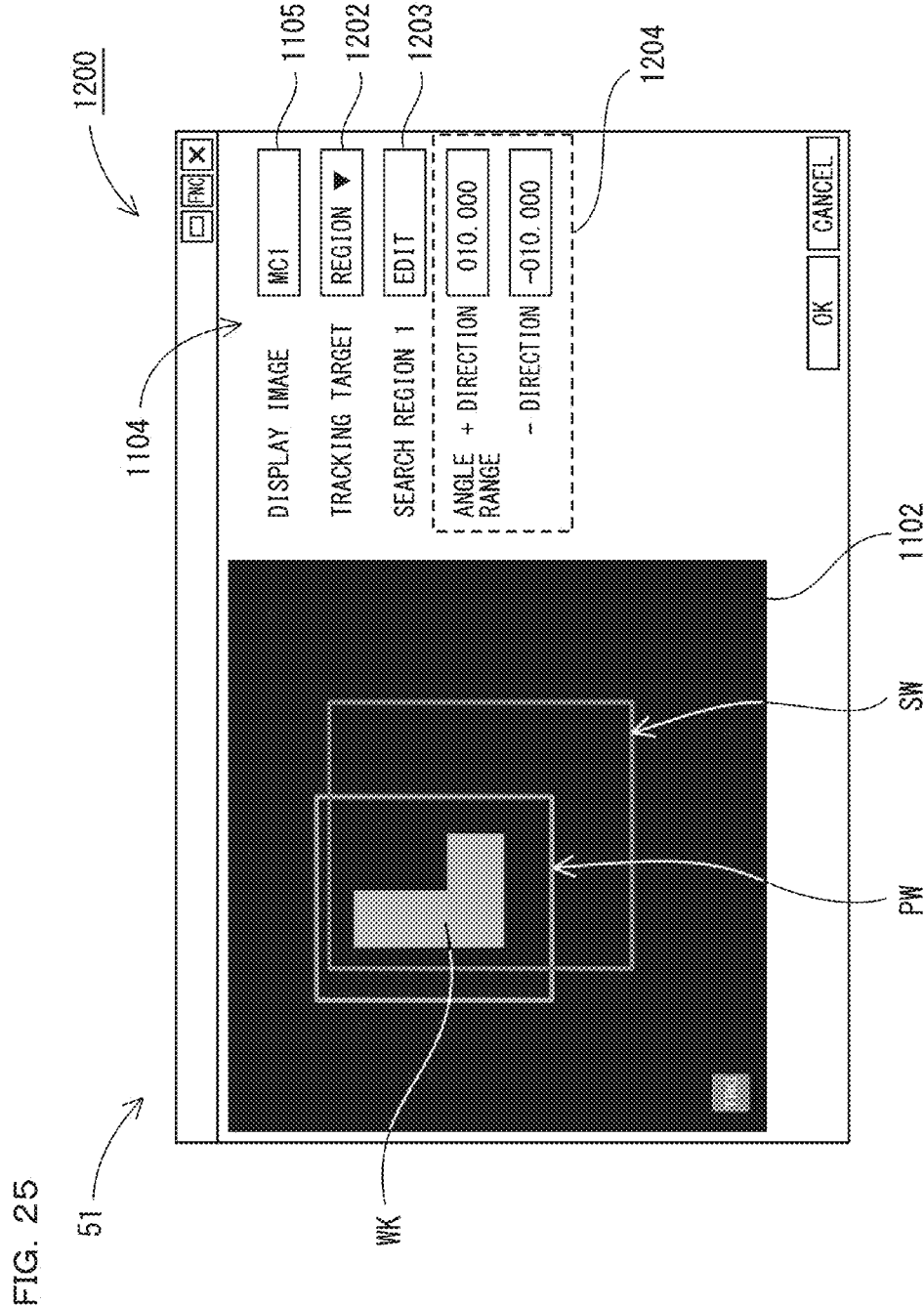
FIG. 25 is a view showing a setting GUI that is displayed in a GUI mainly for the tracking region designating method when an edit button in FIG. 24 is selected.

FIGS. 24 and 25 show one example of a setting section for performing a variety of settings of the image inspection and the image processing. These drawings show one example of a user interface in the image inspection program. Setting screens 1100, 1200 for the image inspection program are displayed on the display section 51 in the image inspection apparatus of FIG. 1, for example. Here, as one example of the setting screen, a screen at the time of setting of "(2) tracking pattern designating method" is shown. The user designates, in these screens, each of the search regions SW1, SW2 and the pattern region PW which are required in the tracking pattern designating method. Further, in the tracking region designating method, the tracking region TW is designated. It is preferable to display each of set regions by changing a display mode so as to allow a plurality of regions to be visually discriminated. In this example, each of the regions is discriminated by a different color. Alternatively, a mode in which discrimination can be performed from other regions, such as a line thickness, a line type (actual line, broken line, dashed line, etc.) or the like can be used as appropriate.

In the setting screens 1100, 1200 shown in FIGS. 24 and 25, an image display region 1102 is provided on the left side of the screen, and an operation region 1104 is provided on the right side of the screen. In the image display region 1102, a variety of screens such as the MC1 image and the MC2 image can be switched and displayed. Further, in the operation region 1104, setting tools for performing a variety of settings are arranged in accordance with the selected screen. In the example shown in FIG. 24, there are provided a display image selection field 1105, a pattern region setting field 1106, a search region 2 setting field 1107, a search sensitivity setting field 1108, a search accuracy setting field 1109, a correlation value lower limit setting field 1110, an angle displacement setting field 1111, a position displacement setting field 1112, and a detailed setting field 1113. In the display image selection field 1105, an image to be displayed in the image display region 1102 can be switched. Here, any of MC1, MC2, PS1, PS2, PS3 and PS4 can be switched and displayed. It is to be noted that the number of PS* images varies depending on the number of PS images used in the photometric stereo processing. Further, the image display region can be divided into a plurality of regions, such as two screens, or a different window can be opened, thereby to display a plurality of images on one screen. In the example of FIG. 24, the MC1 image is displayed.

Further, it is possible to newly set the pattern region PW and the search region SW in pattern region setting field 1106 and in the search region 2 setting field 1107, respectively, or to change the already set region. Here, using a pointing device such as a mouse, an arbitrary region can be designated on the screen of the image display region 1102. For example, a rectangular region can be designated by clicking a diagonal of a rectangular shape. Further, a region can also be designated by a numerical value such as coordinates or an angle range.

Further, the sensitivity of the pattern search can be set in the search sensitivity setting field 1108, and the accuracy of the pattern search can be set in the search accuracy setting field 1109. Here, the sensitivity and the accuracy are designated by numerical values. Moreover, a lower limit of a correlation value can be designated by a numerical value in the correlation value lower limit setting field 1110.

In the angle displacement setting field 1111, the degree of the angle displacement assumed from the linear interpolation angle is set. Here, it may be configured such that a range of the angle displacement is designated by a numerical value, or its degree may be inputted. In this example, as the degree, any of "none", "small", "middle" and "large" is selected from a drop-down box. When "none" is selected, an angle is set to 0°, namely, angle displacement is made nonexistent. When "small" is selected, angle displacement of ±2° is permitted. When "middle" is selected, angle displacement of ±4° is permitted. When "large" is selected, angle displacement of ±6° is permitted In the position displacement setting field 1112, the degree of position displacement assumed from the linear interpolation position is set. Also here, any of "none", "small", "middle" and "large" is selected from a drop-down box. When "none" is selected, only interpolation is applied and position displacement is not permitted. When "small" is selected, a range of ±8 pixels is permitted. When "middle" is selected, a range of ±16 pixels is permitted. When "large" is selected, a range of ±32 pixels is permitted. Further, other than selecting the degree of position displacement as thus described, it may be configured such that the range of position displacement may be directly inputted by units of pixels or by units of length.

Moreover, by pressing an "edit" button in the detailed setting field 1113, the GUI is switched from FIG. 24 to a detailed setting screen 1200 shown in FIG. 25. On the detailed setting screen 1200, in addition to the display image selection field 1105, the operation region 1104 is further provided with a tracking target setting field 1202, a search region 1 setting field 1203 and an angle range setting field 1204. In the search region 1 setting field 1203, a search region 1SW1 can be set or edited similarly to the foregoing search region 2 setting field 1107 and the like. In the tracking target setting field 1202, it is possible to select whether the tracking region TW to become a tracking target in a pattern search is a region or a pattern. In the case of selecting a region, a pattern search is performed using the rectangular tracking region TW designated in the foregoing search region 1 setting field 1203. On the other hand, when a pattern is selected, a shape of the workpiece WK to be tracked, which is included in the tracking region TW, is extracted and a pattern search is performed using the extracted pattern. The extracted pattern is registered as a model image, and at the time of use, a pattern search is performed from the MC1 image. Further, this pattern search includes rotation of the model image. Moreover, in the angle range setting field 1204, an angle range in which the model image is rotated in the pattern search is set. Here, a +direction and a −direction can be respectively designated by numerical values.

In addition, it is desirable to display the MC1 image in the image display region 1102 at the time of setting of the search region SW1, and display the MC2 image therein at the time of setting of the search region SW2. Further, although the image to be displayed in the image display region 1102 can also be selected manually in the display image selection field 1105 and the like, it may be configured such that, when a region to be set is selected, an image suitable for setting of the region is automatically displayed.

Although the setting of "(2) tracking pattern designating method" has been described in the above examples of the setting screens 1100, 1200, it goes without saying that the setting of "(1) tracking region designating method" can also be performed in a similar manner. It is to be noted that in the tracking region designating method, in place of designation of the pattern region PW, the tracking region TW is set.

(3) 1D-Edge Method

Further, as another linear interpolation method, the 1D-edge method in which an edge is used will be described. In the 1D-edge method, the PS* image group is acquired in a state where the workpiece WK is moving similarly to the time of use of the method. A setting is performed while referring to the image group as thus acquired.

(Setting of 1D-Edge Method)

Figure 26:
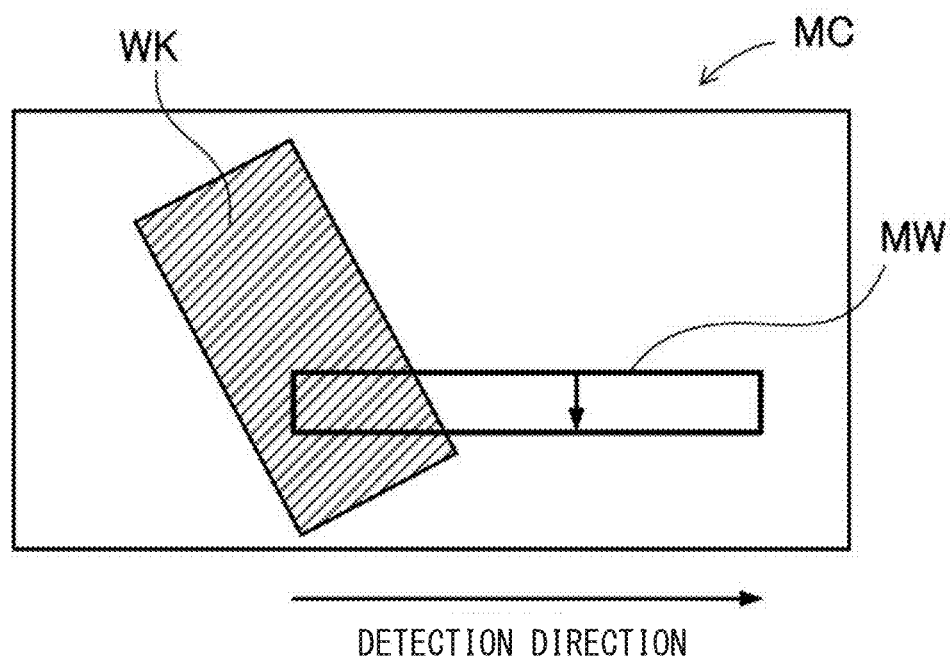
FIG. 26 is a view for use in explaining a setting of a measurement region MW at the time of setting of a 1D-edge method.

In the 1D-edge method, at the time of setting, a measurement region MW, a detection direction, and an edge direction, an edge intensity threshold, and the like are set such that an edge can be detected in all the PS* images. FIG. 26 shows a state of this setting. First, a PS1 image is displayed, and the measurement region MW is set on the PS1 image.

Next, the detection direction is set. The detection direction is set so as to be parallel to the workpiece WK. Further, the edge direction and the edge intensity threshold are set in accordance with characteristics of an edge to be detected. It is to be noted that these settings may be performed with respect to each PS* image.

Here, a final edge index to be detected in the PS4 image is used for designating a final edge. Further, an edge interval is set as a registered edge interval by designating a target edge from a plurality of edge candidates detected in the PS1 image.

(Use of 1D-Edge Method)

A description will be given of an example of using the 1D-edge method in a state where the setting has been performed as described above. At the time of use of the method, a target edge is, found from the PS4 image. This is referred to as a PS4 target edge position. An estimated edge position is calculated from this position and the registered edge interval.

When an edge is detected from the PS1 image, a plurality of edges (candidate edges) may be detected. Among those candidate edges, an edge closer to the estimated edge position is determined as a PS1 target edge position. From this PS1 target edge position and the PS4 target edge position, estimated edge positions of PS2 and PS3 are found by the linear interpolation method. These PS2 target edge position and PS3 target edge position can be computed by a similar technique to that for deciding the PS1 target edge position.

Registration of the PS* image is performed using these pieces of position information. Then, the PS processing is performed using an image group after the registration. Alternatively, the PS processing may be directly performed on the PS* image using these pieces of position information.

In either method, as a method for getting access to pixel information, for example, the nearest neighbor interpolation, bilinear interpolation, bi-cubic interpolation, and the like are known, and these methods are used.

(Setting Screen of 1D-Edge Method)

Figure 27:
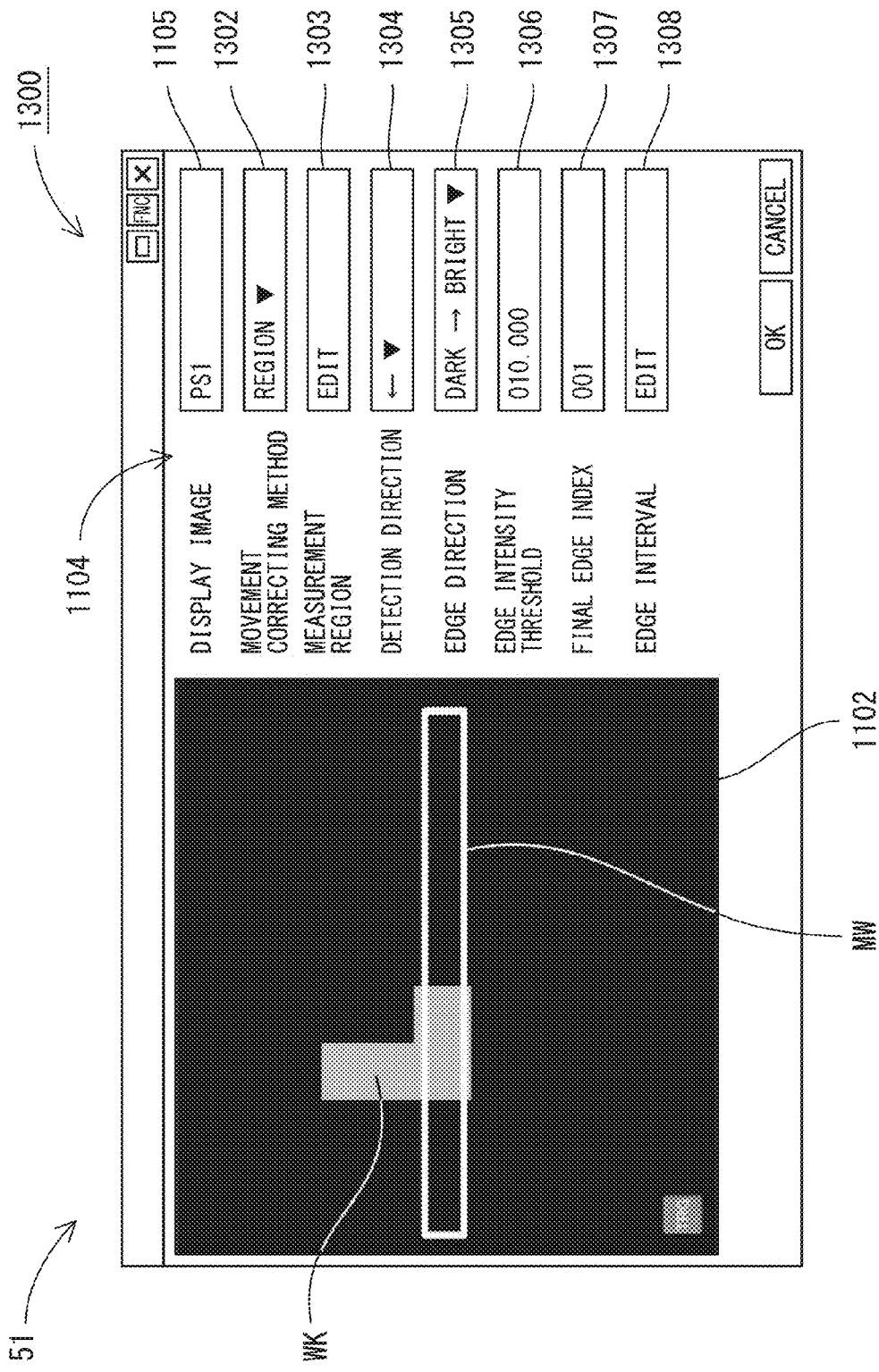
FIG. 27 is a view showing a setting GUI in the 1D-edge method.

Here, FIG. 27 shows one example of a user interface screen of an image inspection program as a setting section for performing a setting in the 1D-edge method. Also in this setting screen 1300, similarly to FIGS. 24 and 25 described above, the image display region 1102 is provided on the left side of the screen, and the operation region 1104 is provided on the right side of the screen. Further, the operation region 1104 is provided with the display image selection field 1105, a movement correcting method setting field 1302, a measurement region setting field 1303, a detection direction setting field 1304, an edge direction setting field 1305, an edge intensity threshold setting field 1306, a final edge index setting field 1307 and an edge interval setting field 1308. In the display image selection field 1105, similarly to FIG. 24 and the like, an image to be displayed in the image display region 1102 can be switched. For example, any of PS1, PS2, PS3 and PS4 can be switched and displayed. In this example, the PS1 image is displayed.

In the movement correcting method setting field 1302, for performing movement correction to be performed by the linear interpolation method, there is selected any of the tracking region designating method which is performed by means of a region, the tracking pattern designating method which is performed by means of a pattern and the 1D-edge method which is performed by means of an edge.

In the measurement region setting field 1303, it is selected whether the edge measurement region MW has a rectangular shape or a rotational rectangular shape.

In the detection direction setting field 1304, it is selected which of "↓", "↑", "→" and "←" is used as an edge detection direction with respect to an image displayed in the image display region 1102. It is to be noted that, when the rotational rectangular shape is selected in the measurement region setting field 1303, this setting becomes unnecessary.

In the edge direction setting field 1305, any of "bright→dark", "dark→bright" and "both" is selected as an edge direction.

In the edge intensity threshold setting field 1306, an edge intensity threshold is standardized and set by a numerical value or the like, when the maximum edge intensity is 999.

An edge position of the PS4 image is designated in the final edge index setting field 1307.

In the edge interval setting field 1308, a first edge of the PS1 image is designated by the pointing device such as the mouse. Further, an edge index may be designated.

The user can perform a setting required for the 1D-edge method from the setting screen 1300.

(Image Transferring Order)

Figure 28:
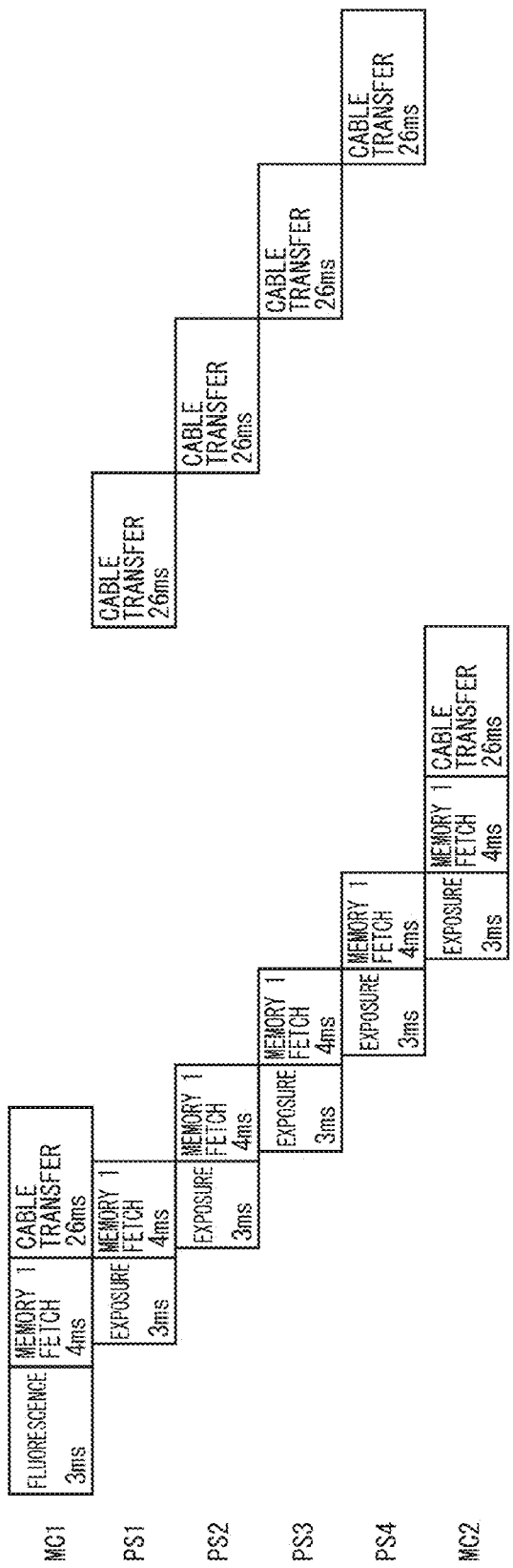
FIG. 28 is a diagram showing an image transfer sequence in the image inspection apparatus according to a first embodiment.
Figure 29:
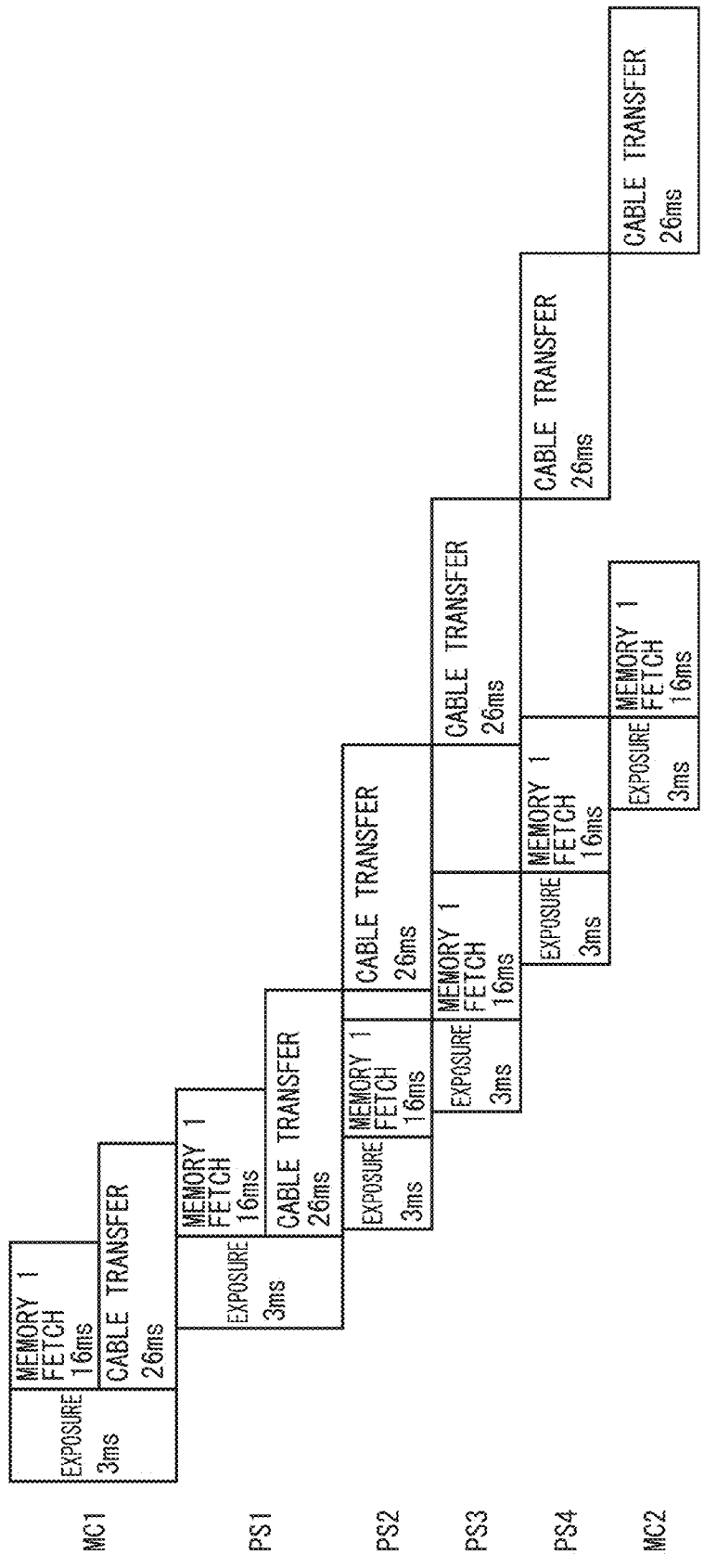
FIG. 29 is a diagram showing an image transfer sequence assumed in a conventional technique.

At the time of implementing any of the foregoing linear interpolation methods, the search region SW is defined for displacement correction in the PS* image by use of information obtained by the searches performed in the MC1 image and the MC2 image. Hence it is desirable to preferentially transfer an image for movement correction to the image processing part 41 as shown in FIG. 28 regardless of the imaging order. This is because, if images are transferred as in the imaging order as shown in FIG. 29, a transfer speed is limited, and hence transfer of the image for movement correction slows down.

(Invalid Pixel)

When the image registration is performed as described above, a pixel corresponding to some pixel in some image may not be included in another image. A pixel of an image calculated by means of a pixel assembly that includes such a non-corresponding pixel in the pixel assembly is herein referred to as an invalid pixel.

Since such an invalid pixel cannot be used for the inspection, at the time of displaying an image that is created by the photometric stereo method, it is desirable to make a display in the same color so as to allow the user to see a status, or make a display of an initial background image. Further, in the case of making a display in the same color, it is desirable to allow the user to select the color.

FIRST MODIFIED EXAMPLE

In the above embodiment, reference images are created at the first and the last of capturing the PS images with respect to a moving body (workpiece) that performs a uniform motion, and an image that matches with the reference image is extracted by the linear interpolation, to establish the image registration.

Figure 30:
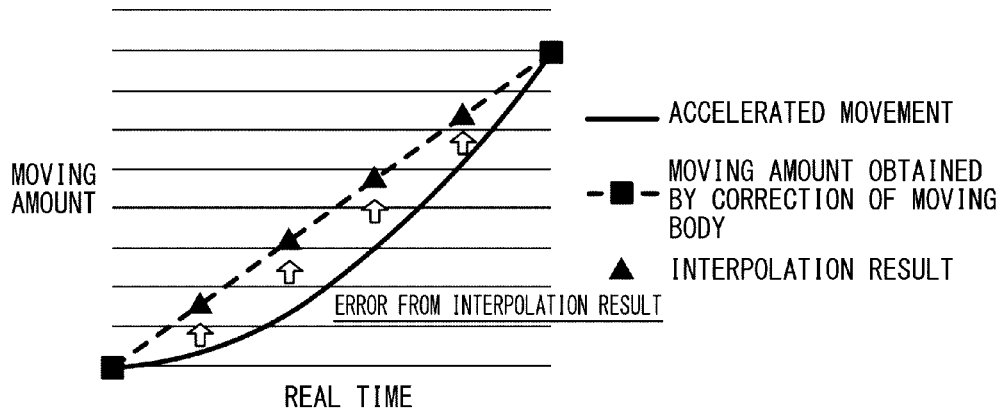
FIG. 30 is a schematic diagram showing a difference of a moving amount in the case of performing linear interpolation on a moving body that performs a uniformly accelerated motion.
Figure 31:
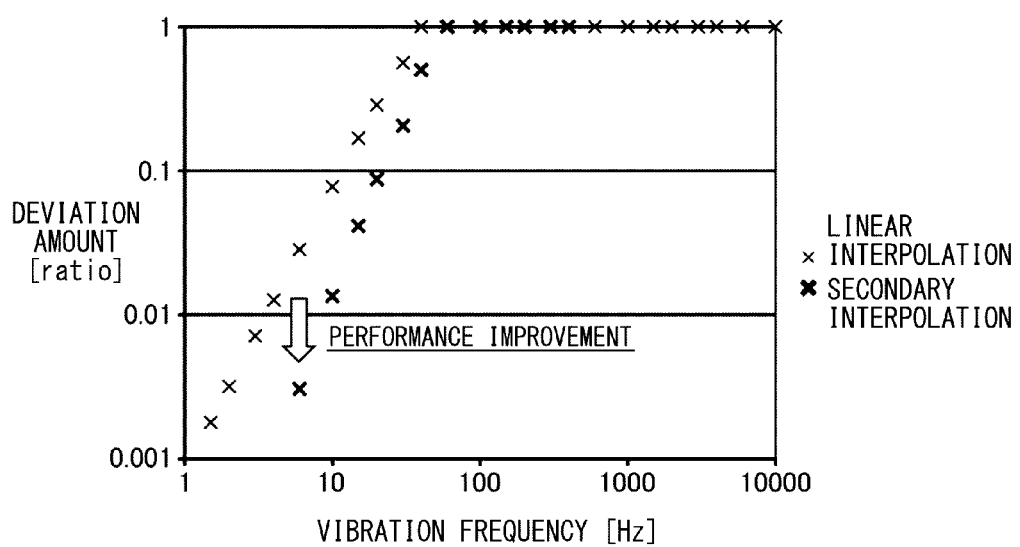
FIG. 31 is a diagram showing a result of assuming one sensor and theoretically calculating an uncorrectable deviation amount in comparison between linear interpolation and secondary interpolation.

However, the present invention is not restricted to the case where the workpiece performs a uniform motion, but approximation such as the linear interpolation or the like can also be applied to a workpiece that shows another motion. For example, when the linear interpolation is performed on a moving body that performs a uniformly accelerated motion, as shown in FIG. 30, a movement amount of movement positions obtained by performing the linear interpolation becomes larger than that of actual movement positions. Although the displacement correction is useful for such a case, the following may be performed in order to enhance the accuracy in estimating the position of the moving body.

For example, a total number of reference images may not be just two, which are created before and after the PS images, but by increasing the number to three or more and performing high-order fitting such as secondary interpolation by means of a function of a position with time also on a moving body that performs a motion other than a uniform motion (e.g., a workpiece that performs a uniformly accelerated motion or vibrates), it is possible to interpolate the position of the workpiece that performs a variety of motions not restricted to the uniform motion and establish the image registration, so as to apply the photometric stereo method.

Figure 32A:
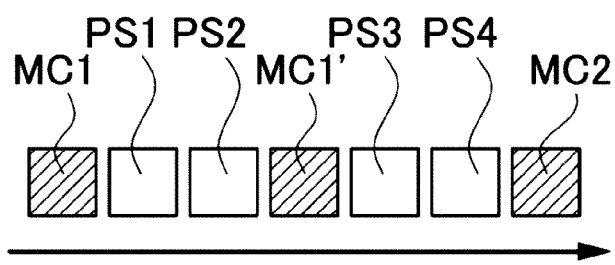
FIG. 32A is a diagram showing the timing for entirely turning-on imaging in four direction illumination of an image inspection apparatus according to a first modified example.

For example, FIG. 32A shows an example where, in a configuration to arrange the foregoing illumination sections in the four directions of north, south, east and west for setting the illumination directions to four directions, capture the PS1 to PS4 images, and capture the entirely turning-on images MC1, MC2 before and after the PS images, the secondary interpolation or the like is performed when the workpiece is a moving body performing a non-uniform motion. FIG. 32A is a diagram showing the timing for entirely turning-on imaging in the case of the four-direction illumination, and in addition to capturing of the entirely turning-on images MC1, MC2 before and after capturing of the PS images as in the embodiment shown in FIG. 19A described above, an operation of also capturing an additional entirely turning-on image MC1' between the MC1 image and the MC2 image is performed. As thus described, images obtained by performing a total of three times of entirely turning-on imaging are regarded as reference images, and the high-order fitting such as the secondary interpolation is performed on each of the partial illumination images. Then, an image that matches with the reference image is extracted from each of the partial illumination images, to establish the image registration.

Figure 32B:
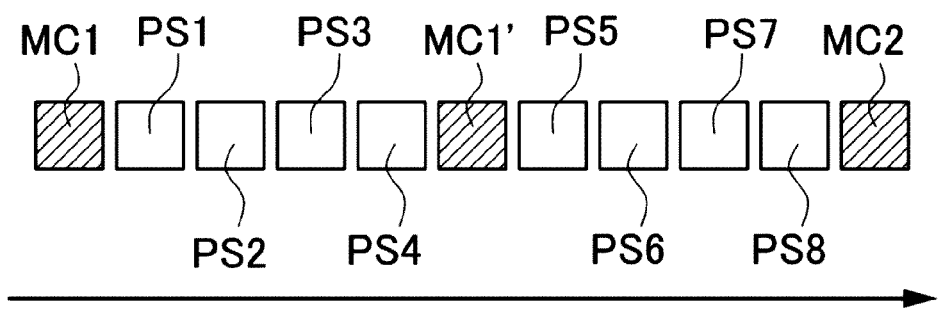
FIG. 32B is a diagram showing the timing for entirely turning-on imaging in eight-direction illumination.

Further, although the example where the number of illumination directions is four has been described in FIG. 32A, the number of illumination directions may be three, or five or more. Also in these cases, it is possible to cope with a non-uniform motion by adding the reference image. For example, FIG. 32B shows an example of making the number of illumination directions be eight by adding four directions of northeast, northwest, southeast and southwest to the four directions of north, south, east and west. Also in this case, by adding the additional entirely turning-on image MC1' as an additional reference image to the middle of the PS images, it is possible to cope with matching of each of the partial illumination images by use of the high-order fitting.

In the above example, the added reference image is interposed in between the MC1 image and the MC2 image. Therefore, the effect of enhancing the accuracy in approximation can be expected. Moreover, the number of reference images including the additional reference image is not restricted to three, but may be increased to a larger number. Especially when the number of PS images is increased, more accurate fitting can be expected by increasing the number of additional reference images to be interposed in the middle of a series of PS images.

Further, in each of the illumination sections, it is preferable to make constant the intensity of illumination light at the time of capturing partial illumination images. This can avoid increasing a luminance difference among the partial illumination images, to allow the photometric processing to be performed with luminance brought closer to uniformity.

Moreover, at the time of turning on all the illumination sections in order to capture an entirely turning-on image, when the number of illumination sections is assumed to be N, the illumination light of each of the illumination sections is preferably adjusted to be 1/N. As thus described, at the time of capturing the entirely turning-on image, uniformly reducing the intensity of the illumination section allows the entirely turning-on image to be captured in an illumination state with a little unevenness. Especially when the workpiece is simultaneously irradiated with strong illumination light from all illumination directions, an overexposed white area is apt to be generated. Accordingly, by intentionally reducing illumination light, it is possible to suppress a light amount such that a tone is not saturated, and to obtain an entirely turning-on image with high quality. Further, it is possible to obtain an advantage of avoiding a state where the entirely turning-on image and the partial illumination image have significantly different brightness and being able to accurately perform arithmetic processing of a corresponding position without unevenness. For example when the number of illumination sections is four, the luminance of illumination light of each of the illumination sections is reduced to ¼ at the time of capturing the entirely turning-on image.

Further, when a motion can be modeled by a special function except for a polynomial expression other than approximation by a high-order function, a parameter is decided from a measurement position in order to uniquely decide the function. Thus, it is possible to estimate a more accurate position and attitude in even a motion that the polynominal expression cannot calculate accurately, so as to realize accurate PS processing.

As thus described, according to the first modified example, by using images obtained by performing three or more times of entirely turning-on imaging as reference images, it is possible to cope with a workpiece that shows a motion other than a uniform motion, such as a uniformly accelerated motion or a vibration motion, so as to realize flaw inspection and OCR of a printed character on a moving workpiece by the photometric stereo method.

SECOND MODIFIED EXAMPLE

Figure 33A:
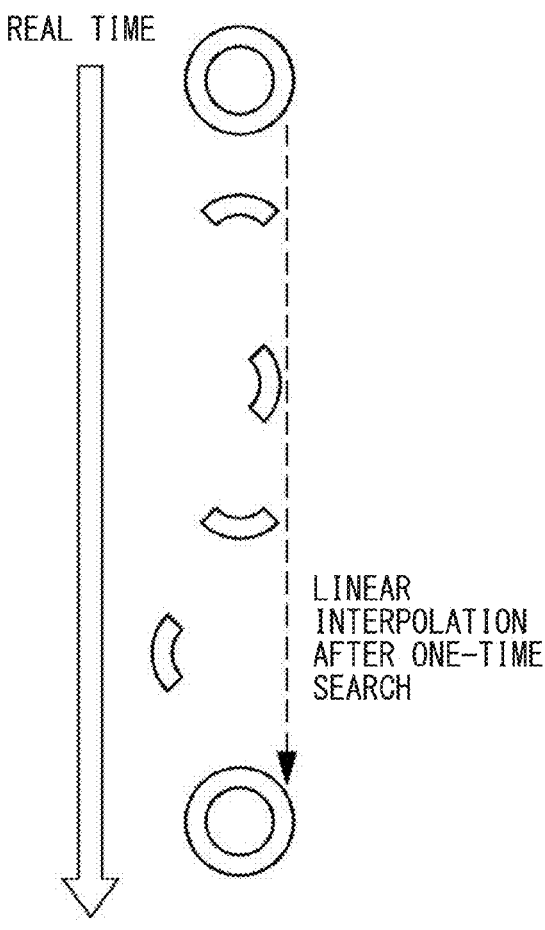
FIG. 33A is an explanatory diagram of imaging timing in the case of monochromatic illumination and is an example in the case of performing entirely turning-on imaging at first and at last.
Figure 33B:
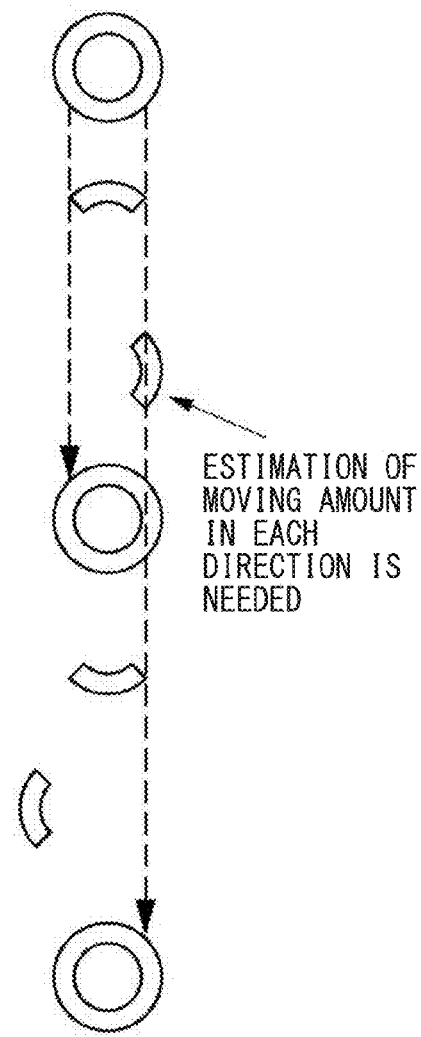
FIG. 33B is an explanatory diagram of imaging timing in the case of monochromatic illumination and is an example in the case of also performing entirely turning-on imaging between the entirely turning-on imaging performed at first and at last.

In the above example, both in the entirely turning-on imaging and each of the partial illumination imaging, irradiation has been performed with, for example, monochromatic while light as illumination light, and the entirely turning-on imaging and each of the partial illumination imaging are performed at different timing. For example, as shown in FIGS. 33A and 33B, in the case of also performing entirely turning-on imaging in between the first and the last, the number of imaging increases by one as compared to the case of performing the entirely turning-on imaging just twice, at the first and the last.

Figure 34:
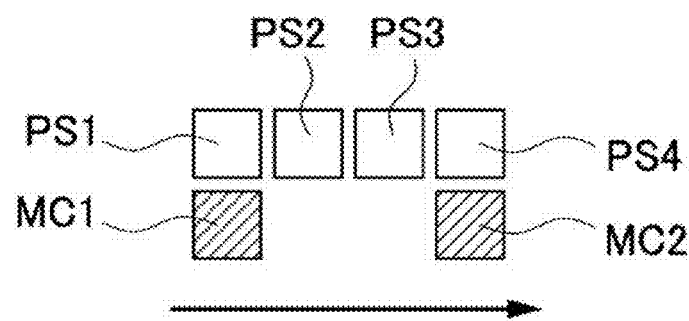
FIG. 34 is a diagram showing four-direction illumination and the timing for four-direction illumination according to a second modified example.
Figure 35:
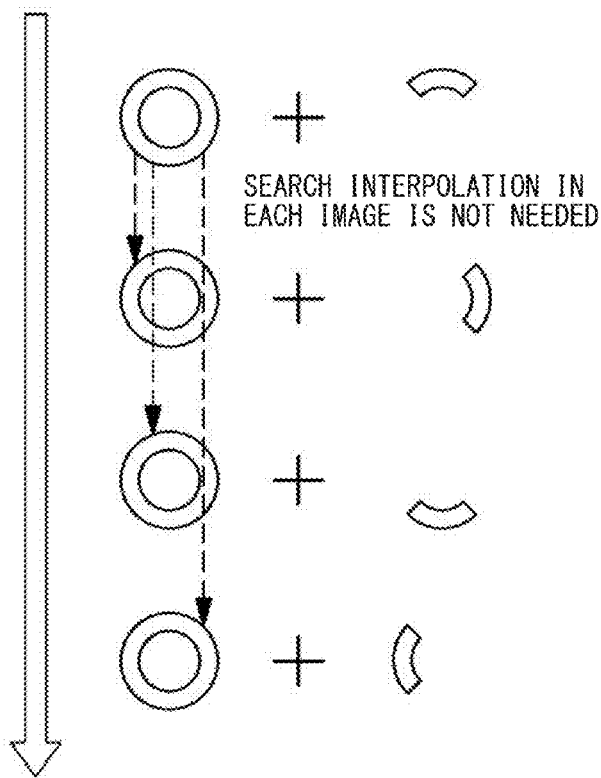
FIG. 35 is an explanatory diagram of imaging timing in the case of color illumination, where a left-side diagram shows entirely turning-on imaging and a right-side diagram shows partial illumination imaging.

The present invention is not restricted to this configuration, and the entirely turning-on image and the partial illumination image may be simultaneously captured. For performing the entirely turning-on illumination and the partial illumination at the same timing, monochromatic light is not used as illumination light, and multicolor light is used. That is, by using color illumination for illumination light emitted by the illumination section, the entirely turning-on imaging and each of the partial illumination can be simultaneously performed as shown in FIG. 34, thereby to reduce the number of times of imaging. For example, as shown in FIG. 35, irradiation is performed with different colors in the first illumination section 21 to the fourth illumination section 24, e.g., illumination light for entirely turning-on illumination is colored red and illumination light of each partial illumination is colored blue, and not a monochromatic image sensor but a color image sensor is used as the imaging section 11. Separating imaging signals detected in the imaging section 11 to the entirely turning-on illumination (e.g., red) and the partial illumination (e.g., blue) allows the entirely turning-on illumination and each of the partial illumination to be simultaneously performed.

The separation of image capturing signals may be performed on a pixel level by the color image sensor, or can be optically performed. Normally in the color image sensor, since color information of RGB is obtained with respect to each pixel, a red entirely turning-on image can be created when only an R component is extracted, and a partial illumination image with each illumination direction can be created when only a B component is extracted.

When the separation is optically performed, there may be used a beam splitter capable of selecting transmitted light, such as a splitter by which red light transmits and blue light is reflected in accordance with wavelengths of the light, and the imaging section 11 having an image capturing element capable of detecting each of the R and B components may be provided on the output side of the beam splitter. Alternatively, an optical filter capable of selectively transmitting light with a specific wavelength, such as a liquid crystal filter, may be arranged at a pre-stage of the imaging section 11, to select and extract reflected light of illumination light by the optical filter.

For discrimination of the first illumination section 21 to the fourth illumination section 24 by colors, for example, a mode as follows can be considered. (1) Examples of combination realized just by separation of each color component includes: (a) green+blue, (b) red+blue and (c) red+green in the case of single colors; and (d) yellow+blue, (e) magenta+green, and (f) cyan+red in the case of mixed colors. (2) Examples of combination that requires linear separation include combinations other than (a) to (f) above. In this case, processing of resolving a non-linear vector is required.

Figure 36:
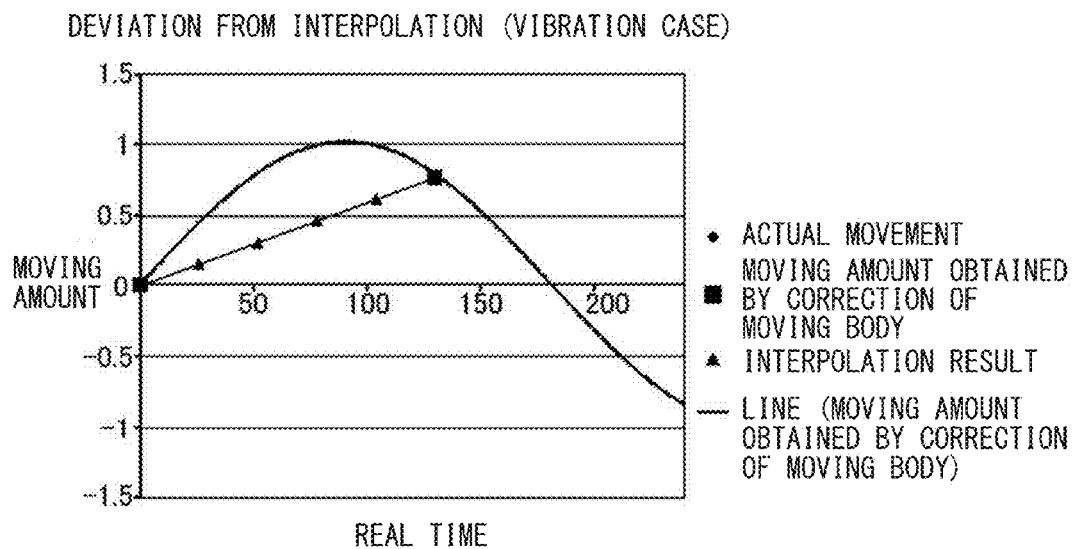
FIG. 36 is a diagram showing a difference of a moving amount generated by linear interpolation when the moving body is vibrating.

When the moving body is performing a complex motion, such as vibrating or performing an irregular motion, as shown in FIG. 36, a large difference can be generated in the moving amount if only the linear interpolation is performed. However, according to the second modified example, the entirely turning-on imaging may not be separately provided at independent timing, saving the time for capturing an additional reference image and reducing the processing time. This is preferable especially for a use in which real-time processing is required, such as line inspection. Further, each partial illumination can be increased by eliminating additional imaging processing, and hence it is possible to improve the accuracy in photometric stereo processing.

Figure 37A:
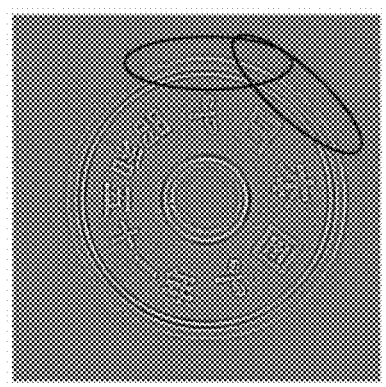
FIG. 37A is an image displaying roughness of a workpiece by means of a Japanese five-yen coin and an example of the case of performing partial illumination imaging from four directions.
Figure 37B:
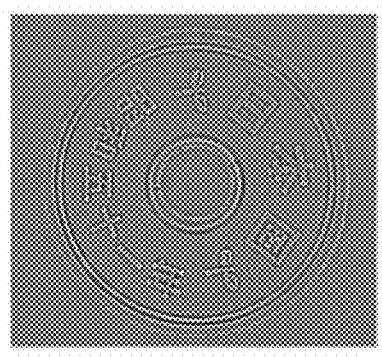
FIG. 37B is an image displaying roughness of the workpiece by means of the coin used for imaging of FIG. 37A and an example of the case of performing partial illumination imaging from eight directions.

Moreover, even in a case where a workpiece reacts to a specific color, depending on characteristics of the workpiece, and a normal vector image is influenced by a luminance value of that color, it is possible to perform illumination while avoiding that color, so as to improve robust characteristics in the inspection. It is to be noted that, depending on the characteristics of the workpiece, a color of illumination can be changed while illumination in a specific color is tested. Thus, it is possible to search a color of illumination which is most suitable for the inspection. For example, although appearance of roughness may be unstable depending on an orientation of a workpiece with strong specular reflection, as shown in FIGS. 37A and 37B, the number of times of turning-on to the partial illumination imaging is increased from the four directions to the eight directions, thereby to stabilize appearance of roughness (e.g. portions surrounded by ellipses) and improve the stability and response capabilities of the inspection.

Further, according to the second modified example, in the case where the photometric stereo method is applied to a workpiece performing a variety of motions as in the first modified example, it is possible to acquire position information of an image extracted from an entirely turning-on image obtained simultaneously with an image with each direction. Thus it can be considered a mode in which a moving amount is not interpolated, and the number of times of imaging can be reduced. Accordingly, it is possible to improve robust characteristics of inspection with respect to a workpiece, imaging timing for which does not catch up with the number of times of imaging when that number is large, such as a workpiece which travels at a high speed or performs an irregular motion.

Moreover, according to the second modified example, since the number of captured images decreases, it is possible to shorten the tact time and reduce an image storing memory.

MODIFIED EXAMPLE 3

Figure 38:
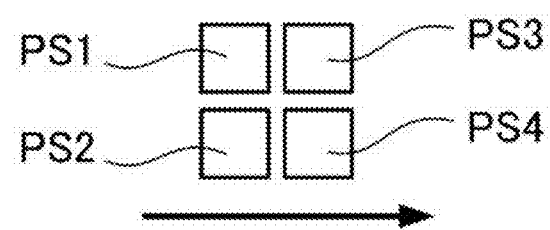
FIG. 38 is a diagram showing the timing for four-direction illumination according to a third modified example.

Further, by changing a wavelength of illumination light, it is also possible to capture partial illumination images at the same timing. That is, not only in the processing of adding a reference image for estimating a position of a moving workpiece or the like, but also in ordinary photometric stereo processing on a workpiece that is still, by simultaneously capturing a plurality of partial illumination images, it is possible to reduce the processing time. For example, as shown in FIG. 38, in the case of capturing four partial illumination images PS1 to PS4 illuminated from four illumination directions, by making different a wavelength of illumination light of each of the first illumination section and the second illumination section, it is possible to capture the partial illumination images PS1 and PS2 at the same timing. Similarly, when a wavelength of illumination light of each of the third illumination section and the fourth illumination section is made different, it is possible to capture the partial illumination images PS3 and PS4 at the same timing. Hence it is possible to reduce the image capturing time in the photometric stereo processing. Further, it is also possible to apply such processing to the interpolation processing on the workpiece of the moving body described above.

According to the present embodiment, there is the special characteristic of repeatedly searching a shape similar to that of a workpiece. In this case, by using a flaw, a stain or the like on the surface of the workpiece as a tracking target image, it can be made useful for tracking a fingerprint and the like. Further, the tracking target image is not restricted to an overall view of the workpiece, but part of the workpiece can be designated, or it is not restricted to the workpiece, but a background of the workpiece or the like can also be used.

(Model Image Approach)

In the above, "(1) linear interpolation approach" has been described. Next, "(2) model image approach" will be described. As described above, at the time of creating a model image in the model image approach, examples of the method include: (A) PS model method; and (B) virtual model method. First, the PS model method will be described.

(4-3. PS Model Method)

A search for the image registration will be performed on the PS image. With a change in illumination is large in the PS image, it is difficult to implement a stable search on all the PS* images just by taking the MC1 image as a model or taking the PS1 image as a model. Therefore, at the time of setting of the PS model method, the illumination direction is changed similarly to the time of use of the method while the workpiece WK is kept still, to acquire the MC* image and the PS* image. These acquired MC* image and PS* image are referred to as a model image group here.

Next, referring to any of the model image group, the pattern region PW or the tracking region TW is set. Here, a partial image corresponding to each of the MC1 image and the PS* image is employed as a model. For example, in the case of performing a search for the image registration by means of the PS1 image, a partial image defined by the registered PS1 image is employed as a model. In such a manner, the image registration can be stably performed even in an image with a large change in illumination. In addition, it is assumed that in this PS model method, a change in attitude of the workpiece WK from the time of registration is small. In inspection conditions where this assumption does not hold, the virtual model method is preferable.

(4-4. Virtual Model Method)

Subsequently, a description will be given of setting and use of the virtual model method as another model image approach.

(Setting of Virtual Model Method)

Also in the setting of the virtual model method, the illumination direction is changed similarly to the time of use of the method while the workpiece WK is kept still, to acquire the MC* image and the PS* image (model image group). Then, referring to any of the model image group, the pattern region PW or the tracking region TW is set. Further, a partial image corresponding to each of the MC1 image and the PS* image is employed as a model.

Moreover, from the PS* image, a weighted normal line image obtained by arranging on an image will be acquired by the following mathematical expression.

$$\rho L \begin{pmatrix} n_x \\ n_y \\ n_z \end{pmatrix}$$ [Mathematical Expression 4]

At the time of use of the method, a model image for search is created from this normal line image.

(Use of Virtual Model Method) (Case of Using Tracking Region Designating Method in Virtual Model Method)

Processing at the time of use of the virtual model method is different between the tracking region designating method and the tracking pattern designating method. In the case of using the tracking region designating method in the virtual model method, similarly to the PS model method, a change in attitude of the workpiece WK from the time of registration is required to be small.

In this case, it is estimated that the weighted normal line image is irradiated with illumination light corresponding to each PS* image, and each estimated pixel value corresponding to the PS* image is calculated by the following mathematical expression.

$$(s_{*x} s_{*y} s_{*z}) \rho L \begin{pmatrix} n_x \\ n_y \\ n_z \end{pmatrix}$$ [Mathematical Expression 5]

Here, an orientation of illumination of the PS* image is expressed by $(S^*_x, S^*_y, S^*_z)$. Using this image, a search is performed on the PS* image.

(Case of Using Tracking Pattern Designating Method in Virtual Model Method)

Next, a description will be given of the case of using the tracking pattern designating method in the virtual model method. In this case, differently from the tracking region designating method, an estimated attitude can be obtained from the MC* image, thus eliminating the assumption that a change in attitude of the workpiece WK from the time of registration is small.

First, the illumination direction corresponding to the PS* image is rotated by an amount corresponding to the estimated attitude. Accordingly, $(S^*_x, S^*_y)$ out of $(S^*_x, S^*_y, S^*_z)$ is changed as influenced by the rotation. For example, when the attitude is rotated 30°, it means to the model that the illumination is rotated −30°.

$(S^*_x, S^*_y)$ is multiplied by this rotational conversion, and an estimated pixel value of the PS* image is calculated by Mathematical Expression 5, to perform a search in the PS* image by use of this image.

Further, it is also possible to use these examples in combination. Specifically, a model image is created by either of the two methods: (A) PS model method where an actually captured image is regarded as a model image; and (B) virtual model method where a virtually created image is regarded as a model image, and an image that matches with the model image is extracted by the linear interpolation or the like, to establish the image registration. Thus, it is possible to acquire an illumination direction from position information of the extracted image.

It is to be noted that, although the example of using as the reference image the entirely turning-on image where all the illumination sections are turned on has been described in the above example, a clear image may be captured even in a state where part of the illumination sections has been turned off, depending on the shape of the workpiece or a reflective state of the surface of the workpiece. Thus, it is possible to use such an image as the reference image. In other words, the reference image is not necessarily restricted to the entirely turning-on image.

The image inspection apparatus, the image inspection method, the image inspection program, and the computer-readable recording medium or the recording device according to the present invention are preferably usable for an inspection apparatus or a digitalizer using photometric stereo.

What is claimed is:

1. An image inspection apparatus for performing visual inspection of a moving workpiece, the apparatus comprising:
   three or more illumination sections for illuminating the workpiece from mutually different illumination directions;
   an illumination controlling section for turning on the three or more illumination sections one by one in a predetermined turning-on order or simultaneously turning on the three or more illumination sections;
   an imaging section for capturing an image of the workpiece from a certain direction at illumination timing for turning on each of the illumination sections by the illumination controlling section, to capture a plurality of partial illumination images with different illumination direction, a first reference image by simultaneously turning on the three or more illumination sections, and a second reference image at imaging timing temporally after the first reference image;

a tracking target image designating section for designating a tracking target image which is included in the first reference image and is used for tracking a position of the workpiece;

a corresponding position estimating section for searching a position of the tracking target image designated by the tracking target image designating section from the second reference image, and specifying a position including the tracking target image in the second reference image, to estimate a corresponding relation of pixels that correspond among each of the partial illumination images based on the specified position; and an inspection image generating section for generating an inspection image for photometric stereo based on the corresponding relation of each of the pixels of the partial illumination images estimated by the corresponding relation estimating section.

2. The image inspection apparatus according to claim 1, wherein at a time of setting prior to the visual inspection of the moving workpiece, the tracking target image designating section designates a tracking region as the tracking target image from the first reference image, and at an operation time when the visual inspection of the moving workpiece is performed, the corresponding relation estimating section specifies a position of an image corresponding to the tracking region from the second reference image by means of the tracking region, to estimate a position of the tracking region in each of the partial illumination images by use of a relative change between the specified position in the second reference image and a position of the first reference image in which the tracking region is designated.

3. The image inspection apparatus according to claim 1, wherein at a time of setting prior to the visual inspection of the moving workpiece, the tracking target image designating section designates a pattern region, and at an operation time when the visual inspection of the moving workpiece is performed, the corresponding relation estimating section employs an image included in the pattern region as a tracking target image and specifies a position of the tracking target image from each of the first reference image and the second reference image, to estimate a position of the tracking target image in each of the partial illumination images by use of a relative change between the specified positions of the tracking target images in the first reference image and the second reference image.

4. The image inspection apparatus according to claim 1, wherein the illumination controlling section completes a cycle of turning-on timing for each of the illumination sections so as to capture, by the imaging section, partial illumination images illuminated from different illumination directions at successive imaging timing, controls the turning-on timing for each of the illumination sections so as to capture reference images before and after the completed cycle of the illumination timing, and controls each of the turning-on timing so as to have a regular interval, and the imaging section synthesizes the imaging timing with the turning-on timing controlled by the illumination controlling section.

5. The image inspection apparatus according to claim 1, further comprising a position displacement amount setting section for setting an assumed position displacement amount between the workpiece and a linearly interpolated workpiece, or an angle displacement amount setting section for setting an assumed angle displacement amount between the workpiece and the linearly interpolated workpiece.

6. The image inspection apparatus according to claim 1, wherein the reference image is an entirely turning-on image captured by the imaging section in a state where all the illumination sections are turned on.

7. The image inspection apparatus according to claim 6, wherein, when the number of the illumination sections is N, illumination light of each of the illumination sections is adjusted to be 1/N at the time of turning on all of the illumination sections so as to capture an entirely turning-on image.

8. The image inspection apparatus according to claim 7, wherein the number of the illumination sections is four, and illumination light of each of the illumination sections is adjusted to be ¼ at the time of turning on all of the four illumination sections for capturing an entirely turning-on image.

9. The image inspection apparatus according to claim 1, wherein the inspection image generating section includes a normal vector calculating section for calculating a normal vector with respect to the surface of the workpiece at each of pixels by a photometric stereo method by use of a pixel value of each of the pixels having the corresponding relation among the plurality of partial illumination images captured by the imaging section, and a contour image generating section for performing differential processing in an X-direction and a Y-direction on the normal vector at each of the pixels calculated by the normal vector calculating section, to generate a contour image that shows a contour of inclination of the surface of the workpiece.

10. The image inspection apparatus according to claim 9, further comprising:

an inspection region specifying section for specifying a position of an inspection region as an inspection target from the contour image generated by the contour image generating section;

an image processing section for performing image processing for detecting abnormality in the inspection region specified by the inspection region specifying section; and a determination section for determining a presence or absence of a flaw on the surface of the workpiece based on a result of the processing by the image processing section.

11. The image inspection apparatus according to claim 1, further comprising:

a texture extraction image generating section for calculating, from a normal vector at each of the pixels which exists in number corresponding to the number of times of illumination performed by the illumination sections and is calculated by the normal vector calculating section, albedos of each of the pixels in the same number as the number of the normal vectors, to generate from the albedos a texture extraction image that shows a design obtained by removing an inclined state of the surface of the workpiece, wherein the contour image generating section and the texture extraction image generating section are configured to be switchable.

12. The image inspection apparatus according to claim 1, wherein the tracking target image is an image including the workpiece.

13. The image inspection apparatus according to claim 1, wherein the normal vector calculating section calculates a normal vector with respect to a workpiece moving at a uniform speed by the photometric stereo method.

14. The image inspection apparatus according to claim 1, wherein the normal vector calculating section calculates a normal vector with respect to a workpiece moving in an X-Y direction by the photometric stereo method.

15. An inspection method for capturing an image of a moving workpiece to perform visual inspection, the method comprising the steps of:
   simultaneously turning on three or more illumination sections at first reference timing, and capturing an image of the workpiece by a common imaging section whose imaging direction and relative position with the illumination section are adjusted in advance, to acquire a first reference image;
   turning on the three or more illumination sections one by one in a predetermined turning-on order, illuminating, from mutually different illumination directions at different turning-on timing, the workpiece moved from the time point of the first reference timing, and capturing one partial illumination image with respect to each illumination direction by the imaging section, to acquire a plurality of partial illumination images with different illumination directions;
   simultaneously turning on the three or more illumination sections at second reference timing, and capturing, by the imaging section, an image of the workpiece further moved from the time point of each of the turning-on timing, to acquire a second reference image;
   designating by a tracking target image specifying section a tracking target image which is included in the first reference image and is used for tracking a position of the workpiece;
   searching the tracking target image designated by the tracking target image designating section from the second reference image, and specifying a position including the tracking target image in the second reference image, to estimate a corresponding relation of pixels that correspond among each of the partial illumination images based on the specified position;
   generating an inspection image for photometric stereo by an inspection image generating section based on the estimated corresponding relation of each of the pixels of the partial illumination images; and
   performing visual inspection of the workpiece by use of the inspection image.

16. An image inspection program embedded in a non-transitory computer readable medium for capturing an image of a moving workpiece to perform visual inspection,
   wherein the program allows a computer to realize functions of:
   simultaneously turning on three or more illumination sections at first reference timing, and capturing an image of the workpiece by a common imaging section whose imaging direction and relative position with the illumination section are adjusted in advance, to acquire a first reference image;
   turning on the three or more illumination sections one by one in a predetermined turning-on order, illuminating, from mutually different illumination directions at different turning-on timing, the workpiece moved from the time point of the first reference timing, and capturing one partial illumination image with respect to each illumination direction by the imaging section, to acquire a plurality of partial illumination images with different illumination directions;
   simultaneously turning on the three or more illumination sections at second reference timing, and capturing, by the imaging section, an image of the workpiece further moved from the time point of each of the turning-on timing, to acquire a second reference image;
   designating a tracking target image which is included in the first reference image and is used for tracking a position of the workpiece;
   searching the designated tracking target image from the second reference image, and specifying a position including the tracking target image in the second reference image, to estimate a corresponding relation of pixels that correspond among each of the partial illumination images based on the specified position;
   generating an inspection image for photometric stereo by an inspection image generating section based on the estimated corresponding relation of each of the pixels of the partial illumination images; and
   performing visual inspection of the workpiece by use of the inspection image.

* * * * *